US011844645B2

(12) United States Patent
Motamed

(10) Patent No.: US 11,844,645 B2
(45) Date of Patent: Dec. 19, 2023

(54) DIAGNOSTIC, MONITORING, AND PREDICTIVE TOOL FOR SUBJECTS WITH COMPLEX VALVULAR, VASCULAR AND VENTRICULAR DISEASES

(71) Applicant: Zahra Keshavarz Motamed, Ancaster (CA)

(72) Inventor: Zahra Keshavarz Motamed, Ancaster (CA)

( * ) Notice: Subject to any disclaimer, the term of this patent is extended or adjusted under 35 U.S.C. 154(b) by 288 days.

(21) Appl. No.: 17/232,606

(22) Filed: Apr. 16, 2021

(65) Prior Publication Data

US 2021/0338192 A1 Nov. 4, 2021

Related U.S. Application Data

(60) Provisional application No. 63/018,675, filed on May 1, 2020.

(51) Int. Cl.
*A61B 8/06* (2006.01)
*A61B 8/08* (2006.01)
*G06T 7/00* (2017.01)
*G16H 50/20* (2018.01)

(52) U.S. Cl.
CPC .............. *A61B 8/06* (2013.01); *A61B 8/0883* (2013.01); *A61B 8/488* (2013.01); *A61B 8/5223* (2013.01); *G06T 7/0012* (2013.01); *G16H 50/20* (2018.01)

(58) Field of Classification Search
CPC ......... A61B 8/06; A61B 8/0883; A61B 8/488; A61B 8/5223; G16H 50/20; G16H 50/50; G06T 7/0012
See application file for complete search history.

(56) References Cited

U.S. PATENT DOCUMENTS

2006/0166176 A1* 7/2006 Lakin ................. G09B 23/12
703/11
2016/0228190 A1* 8/2016 Georgescu ............ A61B 34/10

OTHER PUBLICATIONS

Motamed et al., The role of aortic compliance in determination of coarctation severity: lumped parameter modeling, in vitro study and clinical evaluation, Journal of Biomechanics vol. 48, Issue 16, Dec. 16, 2015, pp. 4229-4237, https://doi.org/10.1016/j.jbiomech.2015.10.017 (Year: 2015).*

Keshavarz-Motamed Z, Garcia J, Pibarot P, Larose E, Kadem L. Modeling the impact of concomitant aortic stenosis and coarctation of the aorta on left ventricular workload. Journal of Biomechanics. 2011; 44:2817-2825 (Year: 2011).*

(Continued)

*Primary Examiner* — John Denny Li
(74) *Attorney, Agent, or Firm* — BERESKIN & PARR LLP/S.E.N.C.R.L., s.r.l.

(57) ABSTRACT

Described are non-invasive methods and associated embodiments for determining an indicator of hemodynamic function using a lumped parameter model of cardiovascular function. The model uses data obtained using a non-invasive cardiovascular imaging modality such as Doppler echocardiography as well as blood pressure data. Various embodiments allow for the diagnosis, monitoring or prognosis of cardiovascular disease including complex valvular, vascular and ventricular diseases (C3VI) as well as prospectively assessing the effect of interventions on cardiovascular function and heart workload.

18 Claims, 22 Drawing Sheets

(56) References Cited

OTHER PUBLICATIONS

Keshavarz-Motamed Z, et al., Non-invasive determination of left ventricular workload in patients with aortic stenosis using magnetic resonance imaging and Doppler echocardiography. PLoS One. Jan. 28, 2014;9(1):e86793. doi: 10.1371/journal.pone.0086793. PMID: 24489786; PMCID: PMC3904946 (Year: 2014).*
Keshavarz-Motamed, Z. et al., "Quantification and systematic differentiation of impact of paravalvular leaks following transcatheter aortic valve replacement." J Am Coll Cardiol. Apr. 2016, 67 (13_Supplement) 2211.
Sotiropoulos, F., Le, T. B. and Gilmanov, A., "Fluid mechanics of heart valves and their replacements." Annu. Rev. Fluid Mech., 2016, 48, 259-283.
Genereux, P. et al., "Paravalvular leak after transcatheter aortic valve replacement: the new Achilles' heel? A comprehensive review of the literature." J. Am. Coll. Cardiol., 2013, 61, 1125-1136.
Nombela-Franco, L. et al., "Significant mitral regurgitation left untreated at the time of aortic valve replacement: a comprehensive review of a frequent entity in the transcatheter aortic valve replacement era." J. Am. Coll. Cardiol., 2014, 63, 2643-2658.
Blanke, P. et al., "Predicting LVOT Obstruction in Transcatheter Mitral Valve Implantation: Concept of the Neo-LVOT." JACC Cardiovasc. Imaging (2016).
Elmariah, S. et al., "Outcomes of Transcatheter and Surgical Aortic Valve Replacement in High-Risk Patients With Aortic Stenosis and Left Ventricular Dysfunction Results From the Placement of Aortic Transcatheter Valves (PARTNER) Trial (Cohort A)." Circ. Cardiovasc. Interv., 2013, 6, 604-614.
Richter, Y. and Edelman, E. R., "Cardiology is flow." Circulation, 2006, 113, 2679-2682.
Zoghbi, W. A., et al., "Recommendations for evaluation of the severity of native valvular regurgitation with two-dimensional and doppler echocardiography." J. Am. Soc. Echocardiogr., 2003, 16, 777-802.
Trip, R., et al., "An experimental study of transitional pulsatile pipe flow." Phys. Fluids 1994-Present, 2012, 24, 014103.
Di Carli, M. F., et al., "The Future of Cardiovascular Imaging." Circulation, 2016, 133, 2640-2661.
Casas, B., et al., "Bridging the gap between measurements and modelling: a cardiovascular functional avatar." Sci. Rep., 2017, 7, 6214.
Duanmu, Z., et al., "A patient-specific lumped-parameter model of coronary circulation." Scientific Reports (2018). doi:10.1038/s41598-018-19164-w.
Marsden, A. L., "Simulation based planning of surgical interventions in pediatric cardiology." Phys. Fluids 1994-Present, 2013, 25, 101303.
Keshavarz-Motamed, Z., et al., "Elimination of trans-coarctation pressure gradients has no impact on left ventricular function or aortic shear stress post intervention in patients with mild coarctation." JACC Cardiovasc. Interv., 2016, 9, 1953-1965.
Taylor, C. A., and Steinman, D. A., "Image-based modeling of blood flow and vessel wall dynamics: applications, methods and future directions." Ann. Biomed. Eng., 2010, 38, 1188-1203.
Omran, H., et al., "Silent and apparent cerebral embolism after retrograde catheterisation of the aortic valve in valvular stenosis: a prospective, randomised study." The Lancet, 2003, 361, 1241-1246.
Elkins, C. J., and Alley, M. T., "Magnetic resonance velocimetry: applications of magnetic resonance imaging in the measurement of fluid motion." Exp. Fluids, 2007, 43, 823-858.
Kilner, P. J., et al., "Flow measurement by magnetic resonance: a unique asset worth optimising." J. Cardiovasc. Magn. Reson., 2007, 9, 723-728.
Chaudhry, Q. A., "A Gaussian function model for simulation of complex environmental sensing." Complex Adapt. Syst. Model., 2015, 3, 3.
Pironet, A., et al., "Simulation of Left Atrial Function Using a Multi-Scale Model of the Cardiovascular System." PLOS ONE, 2013, 8, e65146.
McDowell, S. A. C., "A Simple Derivation of the Boltzmann Distribution." J. Chem. Educ., 1999, 76, 1393.
Mynard, J. P., et al., "A simple, versatile valve model for use in lumped parameter and one-dimensional cardiovascular models." Int. J. Numer. Methods Biomed. Eng., 2012, 28, 626-641.
Broome, M., et al., "Closed-loop real-time simulation model of hemodynamics and oxygen transport in the cardiovascular system." Biomed. Eng. Online, 2013, 12, 69.
Moss, R. L., et al., "Myosin crossbridge activation of cardiac thin filaments: implications for myocardial function in health and disease." Circ. Res., 2004, 94, 1290-1300.
Ferrell, J. E., "Q&A: Cooperativity." J. Biol., 2009, 8, 53.
Stergiopulos, N., et al., "Determinants of stroke volume and systolic and diastolic aortic pressure." Am. J. Physiol., 1996, 270, H2050-2059.
Gleason, W. L., and Braunwald, E., "Studies on the first derivative of the ventricular pressure pulse in man." J. Clin. Invest., 1962, 41, 80-91.
Werf, F. V. de, et al., "Diastolic properties of the left ventricle in normal adults and in patients with third heart sounds." Circulation, 1984, 69, 1070-1078.
Kass, D. A., et al., "Use of a conductance (volume) catheter and transient inferior vena caval occlusion for rapid determination of pressure-volume relationships in man." Cathet. Cardiovasc. Diagn., 1988, 15, 192-202.
Takeuchi, M., et al., "Comparison between preload recruitable stroke work and the end-systolic pressure-volume relationship in man." Eur. Heart J., 1992, 13, 80-84.
Senzaki, H., et al., "Single-beat estimation of end-systolic pressure-volume relation in humans. A new method with the potential for noninvasive application." Circulation, 1996, 94, 2497-2506.
Brown, K. A., and Ditchey, R. V., "Human right ventricular end-systolic pressure-volume relation defined by maximal elastance." Circulation, 1988, 78, 81-91 (1988).
Dell'Italia, L. J., and Walsh, R. A., "Application of a time varying elastance model to right ventricular performance in man." Cardiovasc. Res., 1988, 22, 864-874.
Maniar, H. S., et al., "Impact of pericardial restraint on right atrial mechanics during acute right ventricular pressure load." Am. J. Physiol. Heart Cir. Physiol., 2003, 284, H350-357.
Liang, F., et al., "Multi-scale modeling of the human cardiovascular system with applications to aortic valvular and arterial stenoses." Med. Biol. Eng. Comput., 2009, 47, 743-755.
Tanne, D., et al., "Hemodynamic impact of mitral prosthesis-patient mismatch on pulmonary hypertension: an in-silico study." J. Appl. Physiol., 2008, 105, 1916-1926.
Pibarot, P., et al., "Assessment of paravalvular regurgitation following TAVR: a proposal of unifying grading scheme." JACC Cardiovasc. Imaging, 2015, 8, 340-360.
Feneley, M. P. et al., "Comparison of Preload Recruitable Stroke Work, End-Systolic Pressure-Volume and dP/dtmax-End-Diastolic Volume Relations as Indexes of Left Ventricular Contractile Performance in Patients Undergoing Routine Cardiac Catheterization", JACC vol. 19, No. 7, Jun. 1992: 1522-30.

* cited by examiner (a) Parasternal long axis view of the heart (b) Parasternal short axis view of the heart (c) Apical four-chamber view of the heart (d) Apical five-chamber view of the heart (e) Apical two-chamber view of the heart

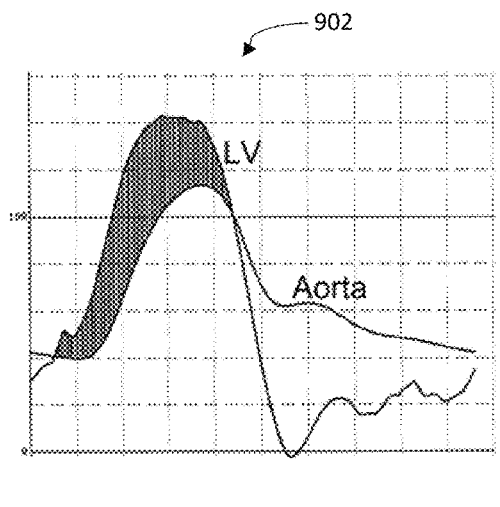
FIG. 9A(i)
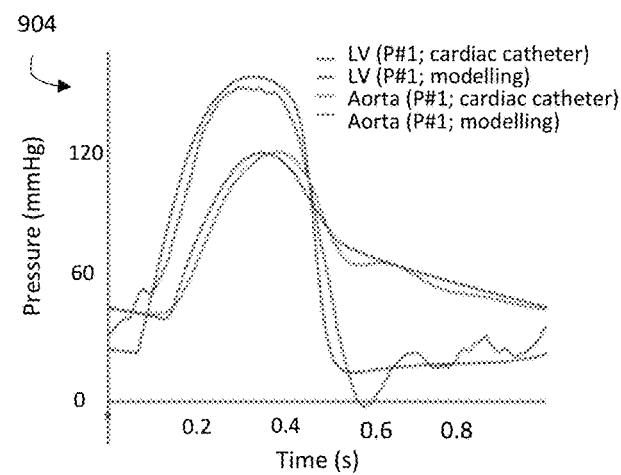
FIG. 9A(ii)
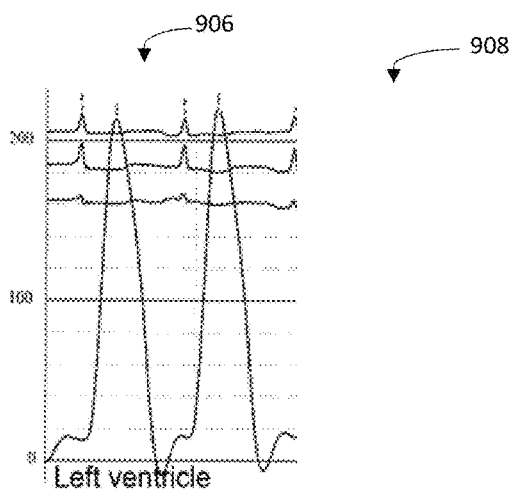
FIG. 9B(i)
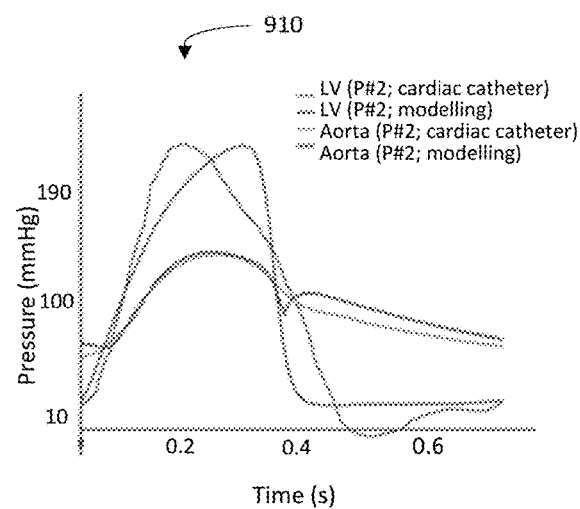
FIG. 9B(ii)

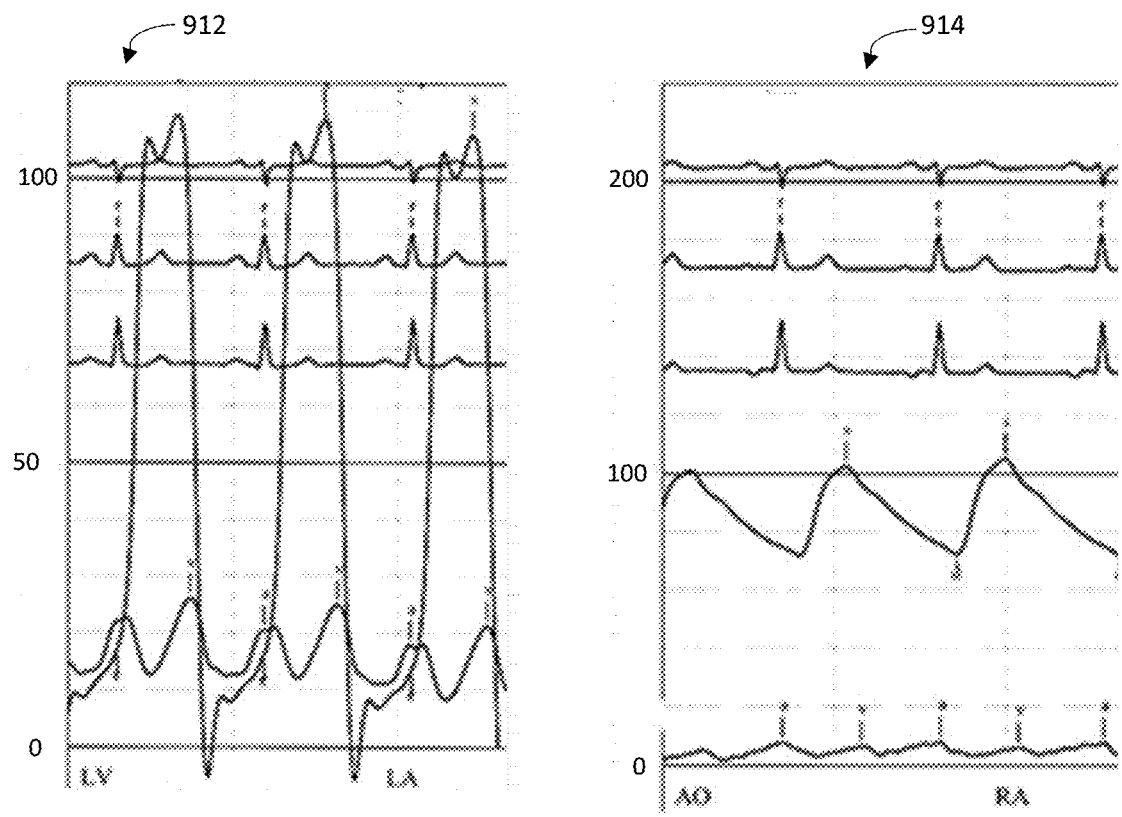
FIG. 9C(i)
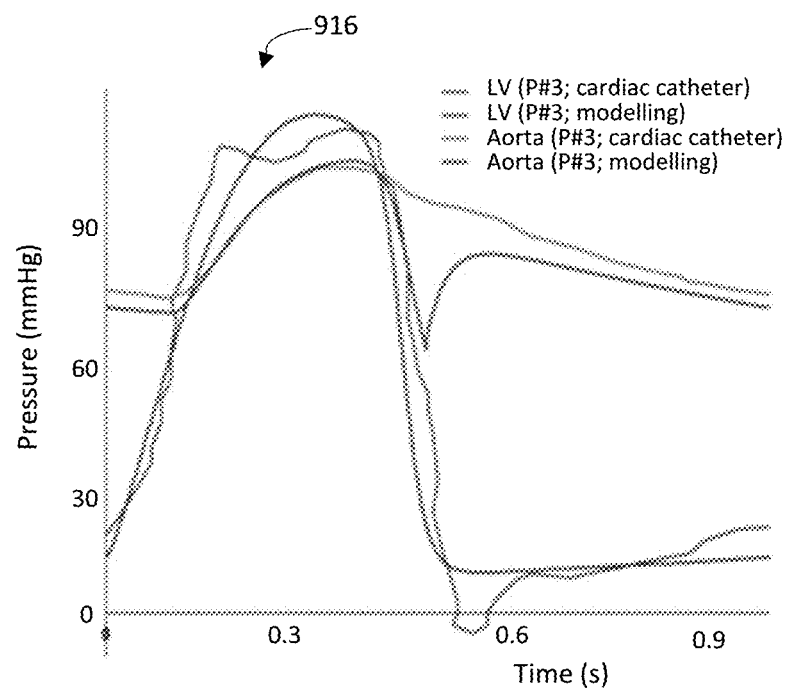
FIG. 9C(ii)

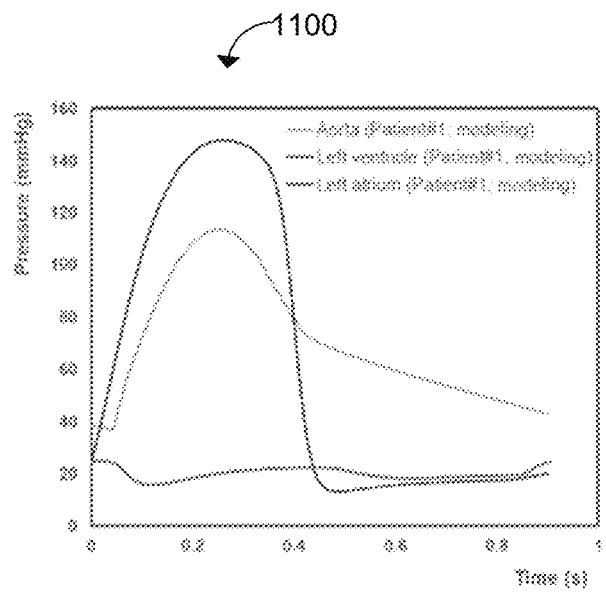
FIG. 11A(i)
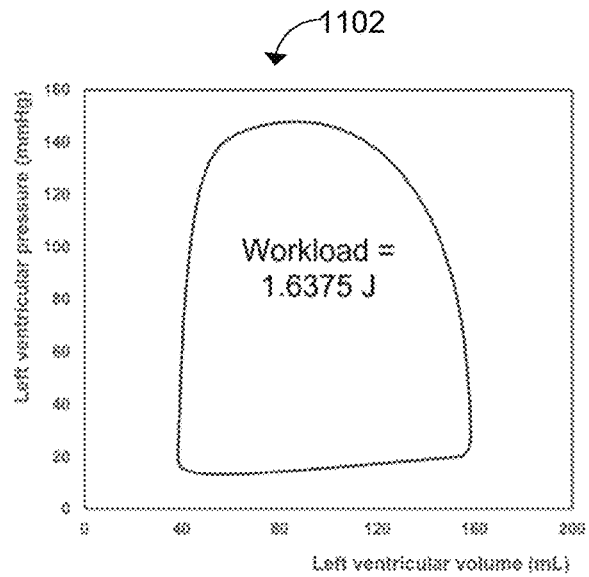
FIG. 11A(ii)
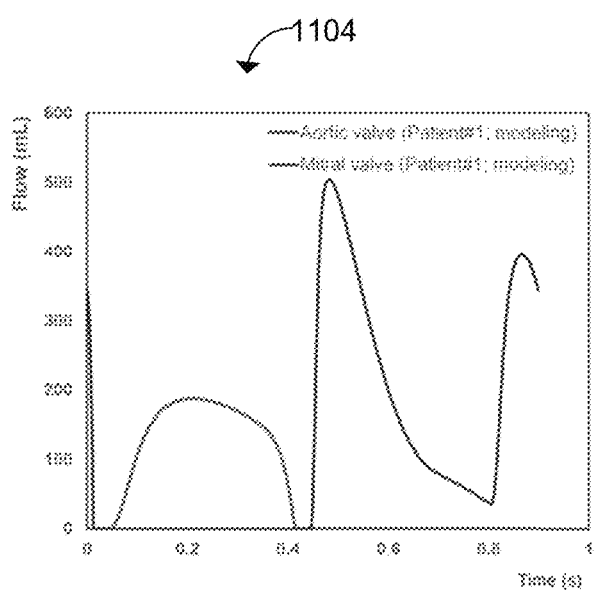
FIG. 11A(iii)
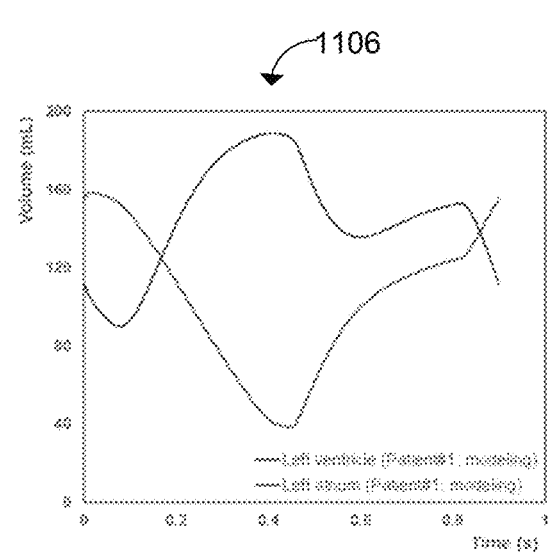
FIG. 11A(iv)

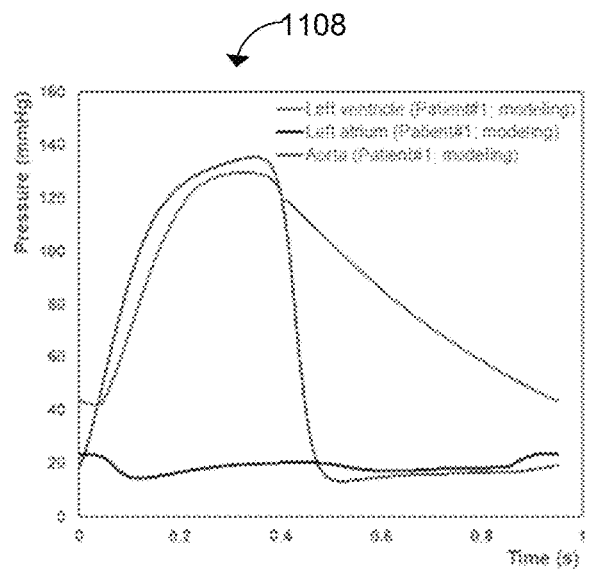
FIG. 11B(i)
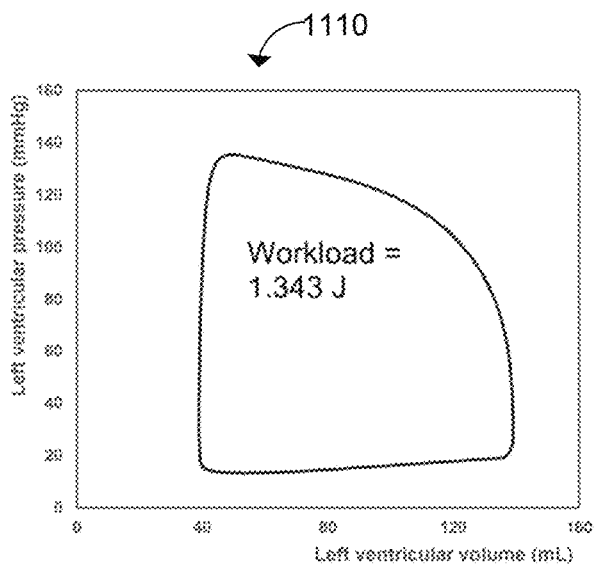
FIG. 11B(ii)
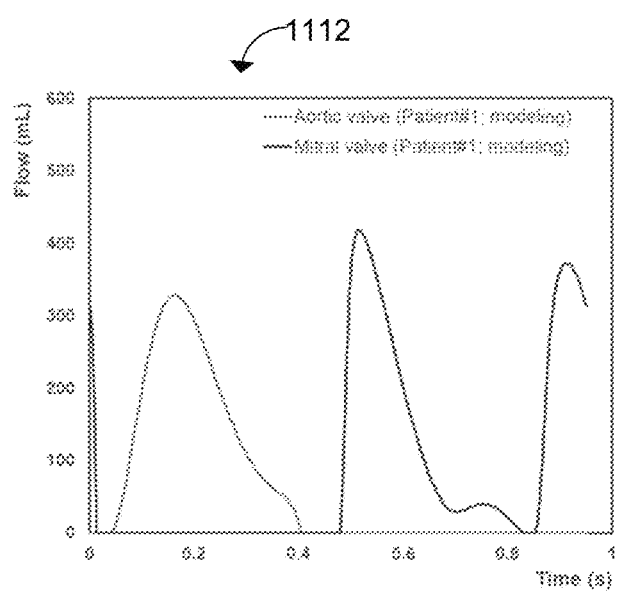
FIG. 11B(iii)
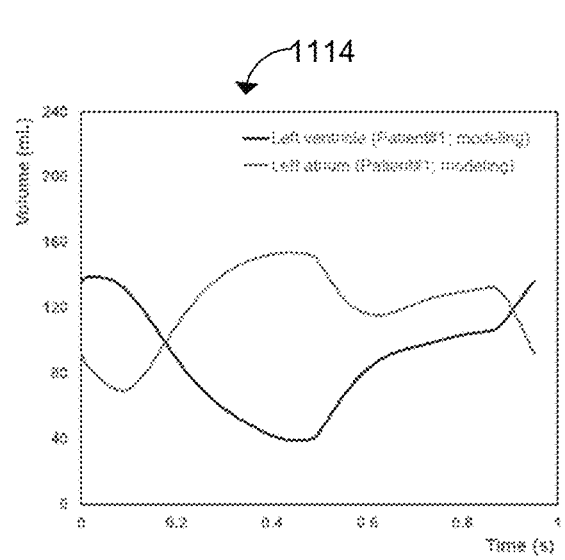
FIG. 11B(iv)

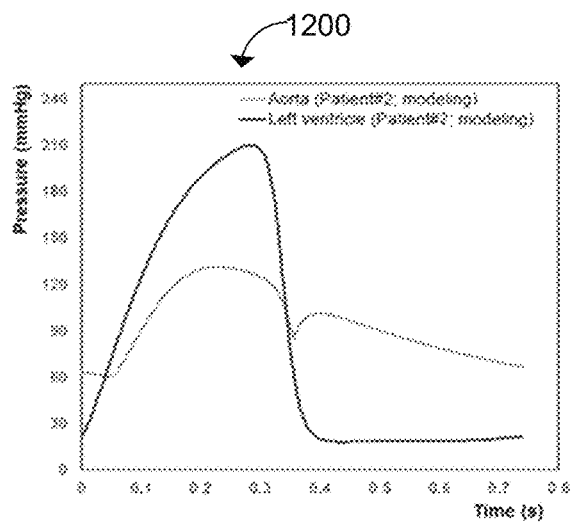
FIG. 12A(i)
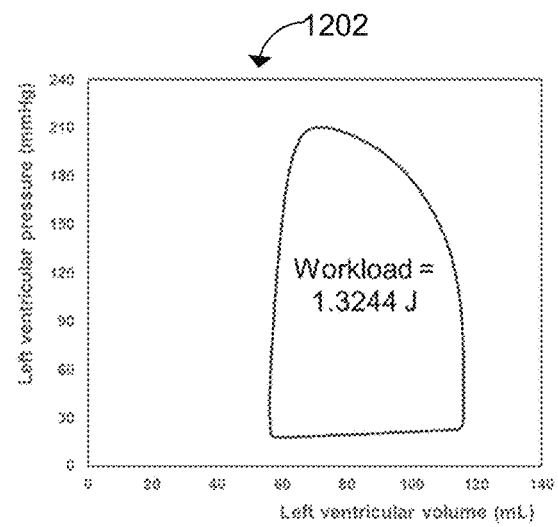
FIG. 12A(ii)
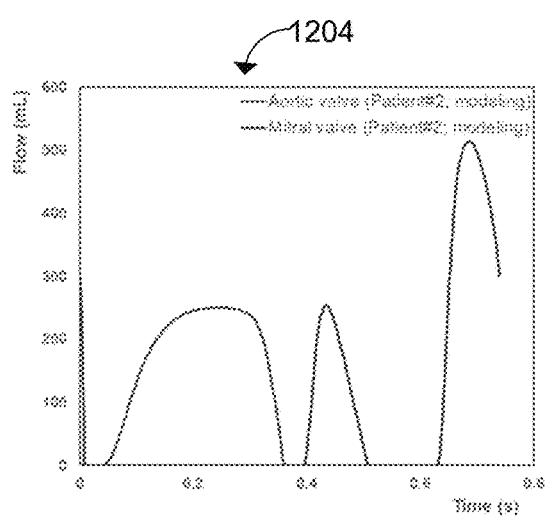
FIG. 12A(iii)
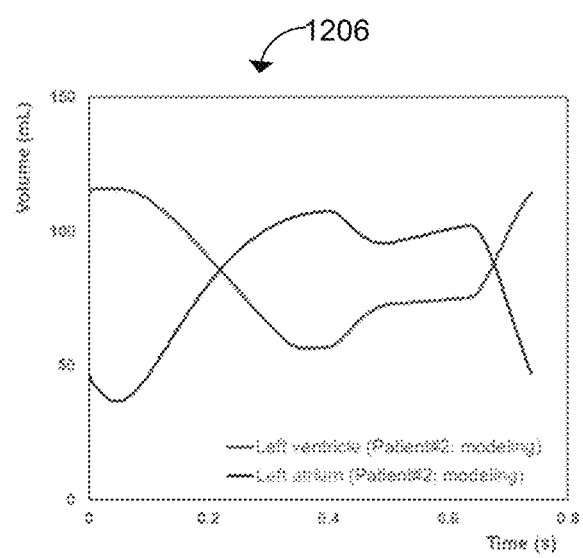
FIG. 12A(iv)

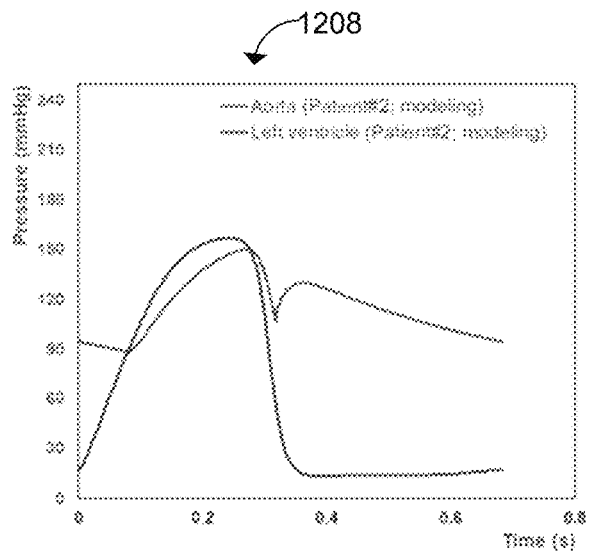
FIG. 12B(i)
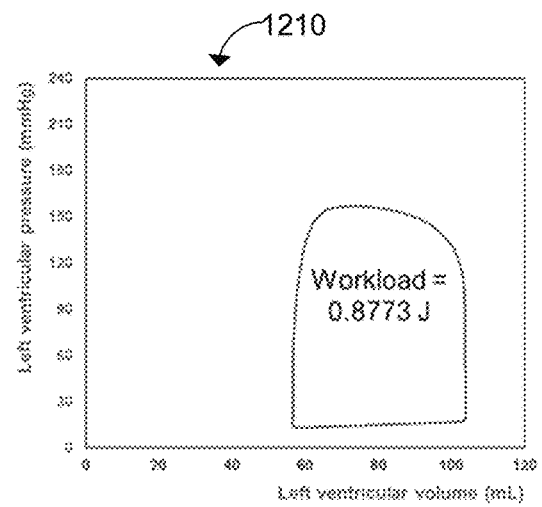
FIG. 12B(ii)
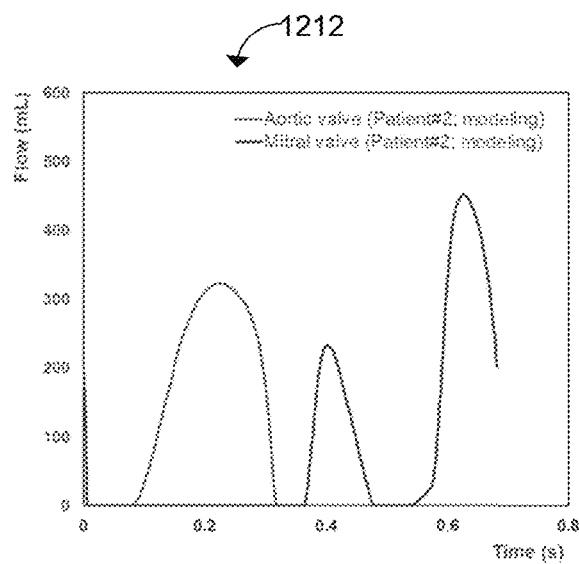
FIG. 12B(iii)
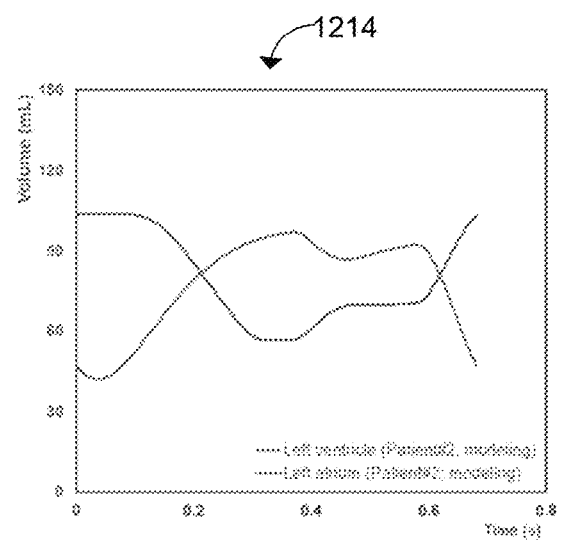
FIG. 12B(iv)

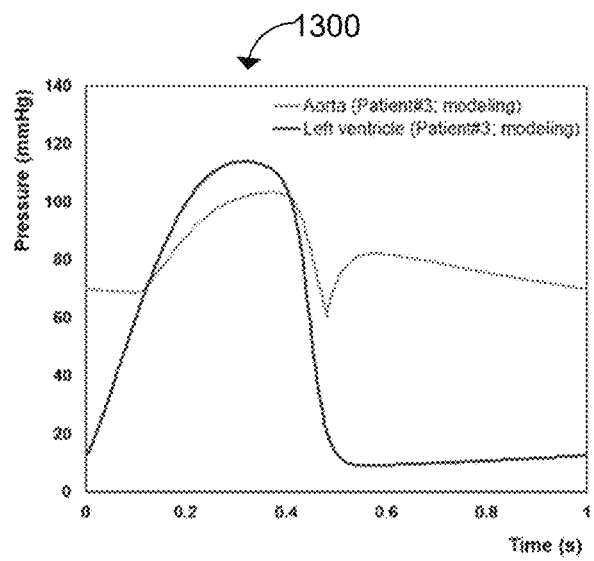
FIG. 13A(i)
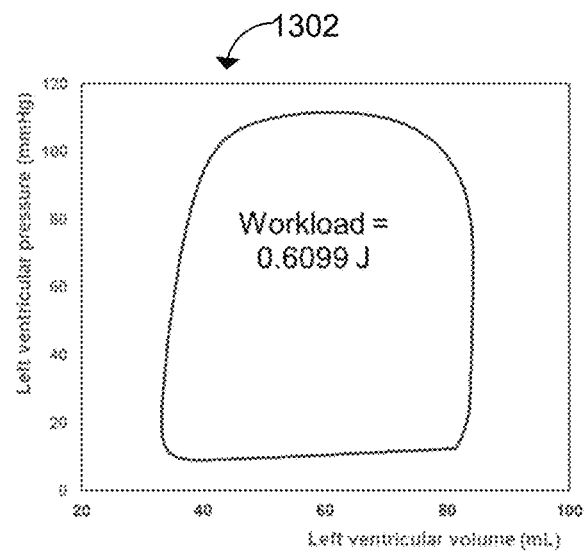
FIG. 13A(ii)
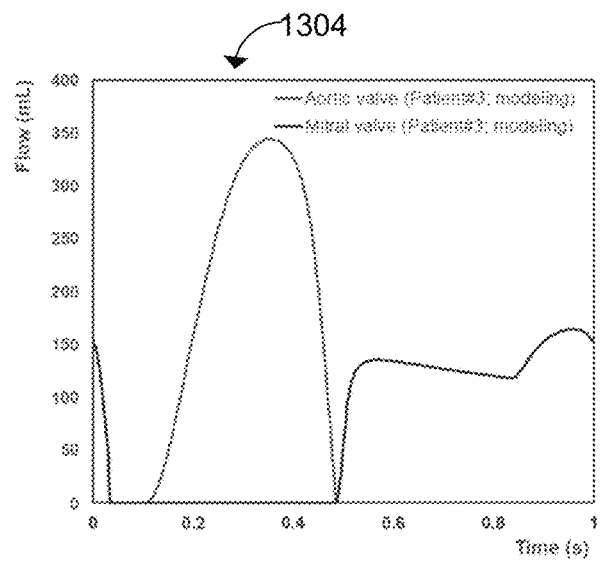
FIG. 13A(iii)
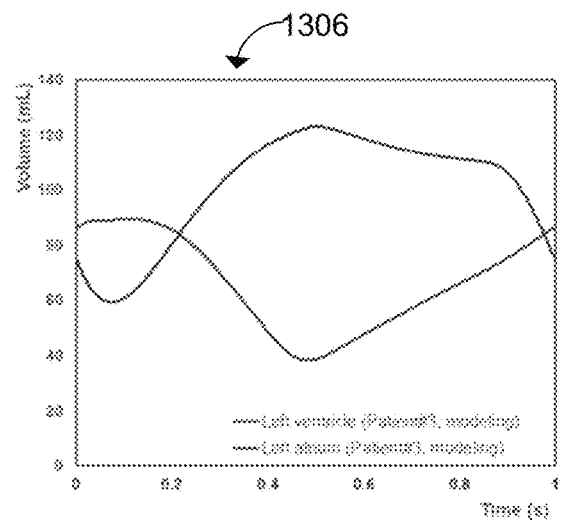
FIG. 13A(iv)

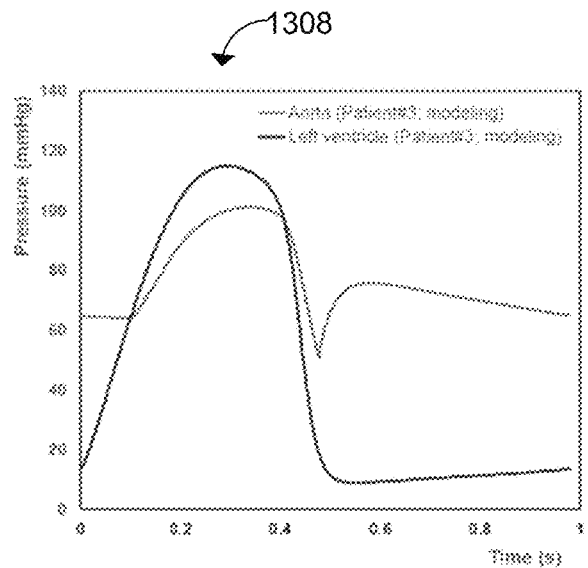
FIG. 13B(i)
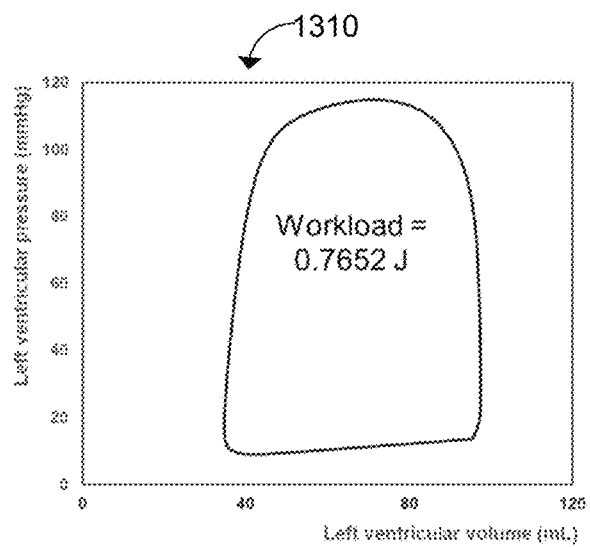
FIG. 13B(ii)
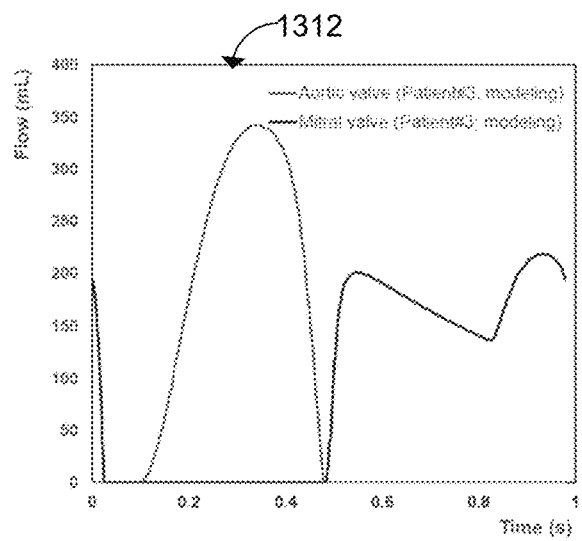
FIG. 13B(iii)
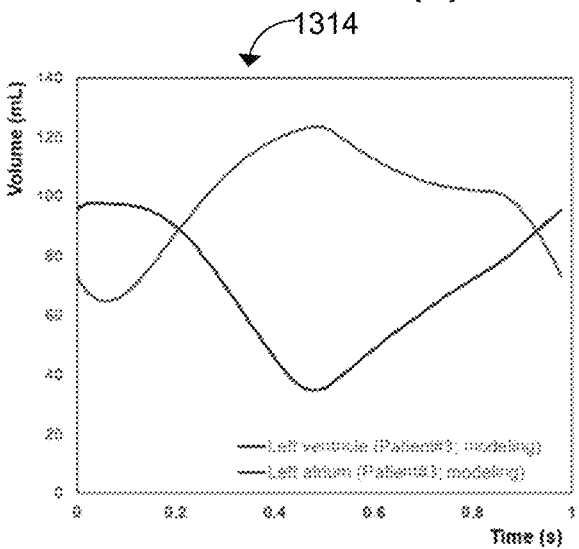
FIG. 13B(iv)

DIAGNOSTIC, MONITORING, AND PREDICTIVE TOOL FOR SUBJECTS WITH COMPLEX VALVULAR, VASCULAR AND VENTRICULAR DISEASES

RELATED APPLICATIONS

This application claims the benefit of priority to U.S. Provisional Application No. 63/018,675 filed May 1, 2020, the entire contents of which are hereby incorporated by reference.

FIELD

The described embodiments relate to cardiovascular disease including complex valvular, vascular and ventricular disease, and more specifically to the use of a lumped parameter model in determining an indicator of hemodynamic function.

BACKGROUND

Cardiovascular disease is the leading cause of death globally, taking more lives than all forms of cancer combined and is the leading cause of burden on healthcare around the world as well. It is expected to remain the first cause of death by 2030 in the worlds. Complex valvular-vascular-ventricular interactions (C3VI) is the most general and fundamentally challenging condition in which multiple valvular, vascular and ventricular pathologies have mechanical interactions with one another wherein physical phenomena associated with each pathology amplify effects of others on the cardiovascular system[2-7]. Examples of components of C3VI include: valvular disease (e.g., aortic valve stenosis, mitral valve stenosis, aortic valve regurgitation and mitral valve insufficiency), ventricular disease (e.g., left ventricle dysfunction and heart failure), vascular disease (e.g., hypertension), paravalvular leaks, and LV outflow tract obstruction in patients with implanted cardiovascular devices such as transcatheter valve replacement (TVR), changes due to surgical procedures for C3VI (e.g., valve replacement and left ventricular reconstructive surgery) and etc.[2,4-7].

"Cardiology is flow"[8]. The main functions of the cardiovascular system are to transport, control and maintain blood flow in the entire body. Abnormal hemodynamics greatly alter this tranquil picture, leading to initiation and progression of disease[9]. These abnormalities are often manifested by disturbed fluid dynamics[10] (local hemodynamics), and in many cases by an increase in the heart workload (global hemodynamics). Hemodynamics quantification can be greatly useful for accurate and early diagnosis but we still lack proper diagnostic methods for many cardiovascular diseases[11-13] because the hemodynamics analysis methods that can be used as engines of new diagnostic tools are not well developed. Furthermore, as most interventions intend to recover the healthy condition, the ability to monitor and predict hemodynamics following particular interventions can have significant impacts on saving lives. Despite remarkable advances in medical imaging, imaging on its own is not predictive[11-14]. Predictive methods are rare. They are extensions of diagnostic methods, enabling prediction of effects of interventions, allowing timely and personalized interventions, and helping critical clinical decision making about life-threatening risks based on quantitative data.

The heart resides in a sophisticated vascular network whose loads impose boundary conditions on the heart function[2,14-16]. Effective diagnosis and prediction hinge on quantifications of the global hemodynamics (heart workload) and of the local hemodynamics (detailed information of the dynamics of the circulatory system, e.g., flow and pressure) of the cardiovascular system as all are very important for long-term health of the heart[2,14,16]. However, there is no method to invasively or noninvasively quantify the heart workload (global hemodynamics) and to provide contribution breakdown of each component of the cardiovascular diseases. Moreover, current diagnostic methods are limited and cannot quantify detailed information of the flow dynamics of the circulatory system (local hemodynamics). Although all of these can provide valuable information about the patient's state of cardiac deterioration and heart recovery currently, clinical decisions are chiefly made based on the anatomy alone with some exceptions. To augment anatomical information, cardiac catheterization is used as the clinical gold standard to evaluate pressure and flow through heart and circulatory system but it is invasive, expensive, high risk and therefore not practical for diagnosis in routine daily clinical practice or serial follow-up examinations[17]. Most importantly, cardiac catheterization only provides access to the blood pressure in very limited regions rather than details of the physiological pulsatile flow and pressures throughout the heart and the circulatory system. Phase-contrast magnetic resonance imaging can provide flow but it has poor temporal resolution, is costly, lengthy and not possible for many patients with implanted devices[18,19]. Doppler echocardiography (DE) is potentially the most versatile tool for hemodynamics as it is low-cost and risk-free and has a high temporal resolution. Despite all the potential of DE and the progress that has been made in its clinical use, to date, there have been no DE methods to comprehensively evaluate local hemodynamics, to evaluate global hemodynamics or to breakdown contributions of each components of the cardiovascular diseases. Computational mechanics has the potential to supplement DE to fill this gap and can offer a powerful means to augment clinical measurements to create non-invasive patient-specific diagnostic and predictive methods for monitoring, treatment planning and risk assessment.

SUMMARY

In one aspect there is provided a non-invasive image-based patient-specific diagnostic, monitoring and predictive computational-mechanics framework (CMF) suitable for determining an indicator of hemodynamic function for a subject. The indicator of hemodynamic function indicative of complex valvular, vascular and ventricular (C3VI) disease. For simplicity, this framework and the associated embodiments for determining an indicator of hemodynamic function in a subject is optionally referred to herein as C3VI-CMF. In some embodiments, embodiments described herein are useful for (1) quantifying details of the physiological pulsatile flow and pressures through the heart and circulatory system (local hemodynamics); and (2) quantifying heart function metrics in terms of the heart workload (global hemodynamics). C3VI-CMF also provides the breakdown of effects of each disease constituents on the global function of the cardiovascular system. C3VI-CMF can also quantify other heart-function metrics such as the left-ventricular end-diastolic pressure and instantaneous left-ventricular pressure. In one embodiment, C3VI-CMF uses input parameters obtained using a non-invasive cardiovascular imaging modality and input parameters indicative of blood pressure. For example, in one embodiment the input parameters are determined using Doppler Echocardiography (DE) and a sphygmomanometer. In one embodiment, the C3VI-CMF comprises a lumped-parameter model at its core and includes several sub-models allowing analysis of hemodynamic function including any combination of complex valvular, vascular and ventricular diseases in both pre and post intervention conditions.

As set out in Example 1 the use of C3VI-CMF was validated against catheterization data in forty-nine patients with C3VI and was demonstrated to correlate well with catheter measurements. For example, using the C3VI-CMF model maximum relative errors of only 4.49% and 4.33% compared to catheterization data were observed for aorta and LV pressures across all forty-nine subjects. Remarkably, while catheterization data can provide data on flow and pressure in specific regions, the systems and methods described herein are also useful for providing details on physiological pulsatile flow and pressure throughout the heart and cardiovascular system. Furthermore, C3VI-CMF is useful for determining indicators of both specific components of hemodynamic function (such as for C3VI disease constituents) as well as global heart workload. This allows for the non-invasive modelling of different interventions for the treatment of C3VI including prioritizing specific interventions based on reducing heart workload. For example, in one embodiment the lumped parameter model determines the indicator of hemodynamic function, and the indicator of hemodynamic function is a prediction of an intervention effect, the prediction of an intervention effect determined based on a determined heart workload (global hemodynamics) and the breakdown of the effects of disease constituents on the global function as well as detailed information of the fluid dynamics of the circulatory system (local hemodynamics).

As shown in FIG. 8 the embodiments described herein may include one or more patient-specific optimization steps following an initial lumped parameter model (LPM) simulation. For example, Doppler echocardiography can reliably measure left ventricular outflow tract stroke volume (LVOT-SV) which can be used to optimize the parameter $Q_{MPV}$, indicative of the mean flow rate of the pulmonary valve. Alternatively or in addition, parameters ($R_{SA}$, $C_{SAC}$ and $C_{ao}$) may be optimized by comparing calculated and measured systolic and diastolic blood pressures. In one embodiment, patient-specific optimization steps are used to (1) calculate the mean flow rate of the pulmonary valve ($Q_{MPV}$) by minimizing the error between the Forward LVOT-SV calculated by the lumped-parameter model and the one measured in each patient using Doppler echocardiography; and (2) adjust the maximum and minimum of the aorta pressures to be equal to or approximate the systolic pressure and diastolic pressure measured using a sphygmomanometer in each patient.

In one aspect, one or more embodiments of the invention provide a non-invasive method for determining an indicator of hemodynamic function for a subject. In one embodiment the method comprises: providing a lumped parameter model, the lumped parameter model comprising a plurality of sub-models, the plurality of sub-models defined by a set of time-varying functions comprising at least one sub-model parameter; receiving a plurality of input parameters for the subject, the input parameters comprising at least one input parameter obtained using a non-invasive cardiovascular imaging modality and at least one input parameter indicative of blood pressure; determining the at least one sub-model parameter in the plurality of sub-models for the subject based on the lumped parameter model and the plurality of input parameters; and optionally determining the indicator of hemodynamic function for the subject based on at least one sub-model parameter for the subject.

In another aspect, one or more embodiments of the invention provide a system for determining an indicator of hemodynamic function for a subject. In one embodiment, the system comprises: a memory, the memory comprising: a lumped parameter model, the lumped parameter model comprising a plurality of sub-models comprising at least one sub-model parameter, the plurality of sub-models defined by a set of time-varying functions of comprising the at least one sub-model parameter; a processor in communication with the memory, the processor configured to: receive a plurality of input parameters for the subject, the input parameters comprising at least one input parameter obtained using a non-invasive cardiovascular imaging modality and at least one input parameter indicative of blood pressure; determine the at least one sub-model parameter in the plurality of sub-models for the subject based on the lumped parameter model and the plurality of input parameters; and optionally determine the indicator of hemodynamic function for the subject based on at least one sub-model parameter for the subject.

In another aspect, one or more embodiments of the invention provide a non-transitory computer readable medium comprising computer-executable instructions for determining an indicator of hemodynamic function for a subject. In one embodiment, the computer-executable instructions when executed cause a processor to determine the indicator of hemodynamic function based on a lumped parameter model and a plurality of input parameters for the subject, the lumped parameter model comprising a plurality of sub-models, the plurality of sub-models defined by a set of time-varying functions comprising at least one sub-model parameter, and the plurality of input parameters for the subject comprising at least one input parameter obtained using a non-invasive cardiovascular imaging modality and at least one input parameter indicative of blood pressure. In one embodiment, the computer-executable instructions when executed cause the processor to determine at least one sub-model parameter in the plurality of sub-models for the subject and determine the indicator of hemodynamic function for the subject based on the at least one sub-model parameter for the subject.

In one or more embodiments, the input parameters obtained using the non-invasive cardiovascular imaging modality may comprise one or more cardiovascular anatomical or functional measurements, optionally obtained using Doppler echocardiography. For example, in one embodiment, the input parameters comprise at least one selected from the group of a forward left ventricular outflow tract stroke volume (LVOT-SV), a heart rate, an ejection time, an ascending aorta area, a left ventricular outflow tract area, an aortic valve effective orifice area, a mitral valve effective orifice area, an indicator of aortic valve regurgitation severity and an indicator of mitral valve regurgitation severity.

In one or more embodiments, the at least one input parameter indicative of blood pressure may comprise a diastolic blood pressure and a systolic blood pressure, optionally obtained using a sphygmomanometer.

In one or more embodiments, the lumped parameter model comprises a plurality of sub-models defined by a set of time-varying functions that model cardiovascular function. In one embodiment, the set of time varying functions comprise one or more sub-model parameters. Optionally, one or more sub-model parameters in the lumped parameter model are optimized by reference to empirically determined data for the subject such as imaging data and/or blood pressure data.

For example, in one embodiment one of the sub-models is a pulmonary circulation sub-model, optionally defined by a rectified sine curve waveform with a duration ($t_{ee}$) and amplitude based on a mean flow rate of the pulmonary valve ($Q_{MPV}$). In one embodiment, a sub-model parameter for the mean flow rate of the pulmonary valve ($Q_{MPV}$) may be optimized based on minimizing the error between a sub-model parameter value of LVOT-SV determined for the subject using the lumped parameter model and a value of LVOT-SV for the subject determined using the non-invasive cardiovascular imaging modality.

Alternatively or in addition, one of the sub-models may be a systemic sub-model, optionally wherein the systemic sub-model is defined by sub-model parameters for systemic artery resistance ($R_{SA}$), aorta compliance ($C_{ao}$) and systemic compliance ($C_{SAC}$).

In one embodiment, sub-model parameter values for systemic artery resistance ($R_{SA}$), aorta compliance ($C_{ao}$) and systemic compliance ($C_{SAC}$) may be optimized based on minimizing the error between values of systolic and diastolic blood pressure determined for the subject using the lumped parameter model and values of systolic and diastolic blood pressure for the subject determined using a sphygmomanometer or another suitable device for measuring blood pressure.

The embodiments described herein are useful for determining an indicator of hemodynamic function. The indicator of hemodynamic function may itself be a sub-model parameter or may be based on one or more sub-model parameters.

In one embodiment, the indicator of hemodynamic function is an indicator of global hemodynamic function. For example, the indicator of global hemodynamic function may be an indicator selected from the group of a left ventricle workload, a left-ventricular end-diastolic pressure, an instantaneous left-ventricular pressure and combinations thereof.

In one embodiment, the indicator of hemodynamic function may comprise an indicator of local hemodynamic function. For example, the indicator of local hemodynamic function may be an indicator selected from the group of a left ventricle pressure, an aorta pressure, an atrium pressure, an aortic valve pressure, a mitral valve pressure, a mitral flow rate, a left ventricle flow, an aorta flow, a left ventricle volume and a left atrial volume as well as flow, pressure and volume through the circulatory system;

In one embodiment, the indicator of hemodynamic function may be an indicator of heart workload. For example, the indicator of heart workload may be an integral of LV pressure and volume estimated as the area covered by a LV pressure-volume loop.

In one or more embodiments, the method may further comprise diagnosing, monitoring or prognosing cardiovascular disease in the subject based on the indicator of hemodynamic function, optionally based on a plurality of indicators of hemodynamic function.

In one or more embodiments, the method may further comprise determining the relative contribution of one or more disease constituents to cardiovascular disease in the subject, optionally by comparing LV workload under different conditions of the lumped parameter model by varying values of one or more sub-model parameters.

In one or more embodiments, the method comprises determining an indicator of hemodynamic function that is a prediction of an intervention effect, such as a surgical intervention, for the subject. In one embodiment, the method comprises determining the indicator of hemodynamic function based on one or more of an indicator of global hemodynamic function determined for the subject, optionally heart workload, a relative contribution of one or more one disease constituents to the indicator of global hemodynamic function for the subject and an indicator of local hemodynamic function determined for the subject. In one embodiment, the indicator of local hemodynamic function provides information on the fluid dynamics of the circulatory system for the subject.

In one or more embodiments, the method may further comprise selecting a treatment for the subject based on the indicator of hemodynamic function, optionally based on a plurality of indicators of hemodynamic function, or based on the relative contribution of the one or more C3VI disease constituents to cardiovascular disease in the subject. Optionally, the method further comprises treating cardiovascular disease in subject with the selected treatment.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

One or more embodiments will now be described in detail with reference to the drawings, in which:

FIG. 3B showing left ventricular outflow tract velocity time integral, taken as the average of the areas; FIG. 3C showing ascending aorta diameter, measured in the parasternal long axis view; and FIG. 3D showing aorta velocity time integral, taken as the average of the areas.

FIG. 4A shows a parasternal short axis view. FIG. 4B shows a parasternal long axis view.

FIG. 5A shows Mitral valve diameter ($d_1$), measured in apical two-chamber view; FIG. 5B shows Mitral Valve diameter ($d_2$), measured in apical four-chamber view.

FIGS. 7A and 7B show an end of systole LV volume in apical four-chamber view and apical two chamber view respectively. FIGS. 7C and 7D show an end of diastole LV volume in apical four-chamber view and apical two-chamber view respectively.

FIGS. 9A(i), 9A(ii), 9B(i), 9C(i), 9C(ii) shows a pressure waveform comparison, in accordance with one or more embodiments. FIGS. 9A(i) and 9A(ii) may be for a first subject, FIGS. 9B(i) and 9B(ii) may be for a second subject, and FIGS. 9C(i) and 9C(ii) may be for a third subject.

FIG. 10A shows the peak pressure correlation diagram for the left ventricle. FIG. 10B shows the peak pressure correlation diagram for the aorta.

FIGS. 11A(i), 11A(ii), 11A(iii), 11A(iv), 11B(i), 11B(ii), 11B(iii) and 11B(iv) are examples of predicted hemodynamics in a C3VI patient (Sample case #1) from baseline to 90 days post-TAVR, in accordance with one or more embodiments.

FIGS. 12A(i), 12A(ii), 12A(iii), 12A(iv), 12B(i), 12B(ii), 12B(iii) and 12B(iv) show examples of predicted hemodynamics in a C3VI patient (Sample case #2) from baseline to 90 days post-TAVR, in accordance with one or more embodiments.

FIGS. 13A(i), 13A(ii), 13A(iii), 13A(iv), 13B(i), 13B(ii), 13B(iii) and 13B(iv) show examples of predicted hemodynamics in a C3VI patient (Sample case #3) from baseline to 80 days post-valvuloplasty, in accordance with one or more embodiments.

DESCRIPTION OF EXEMPLARY EMBODIMENTS

Definitions

Figure 1A:
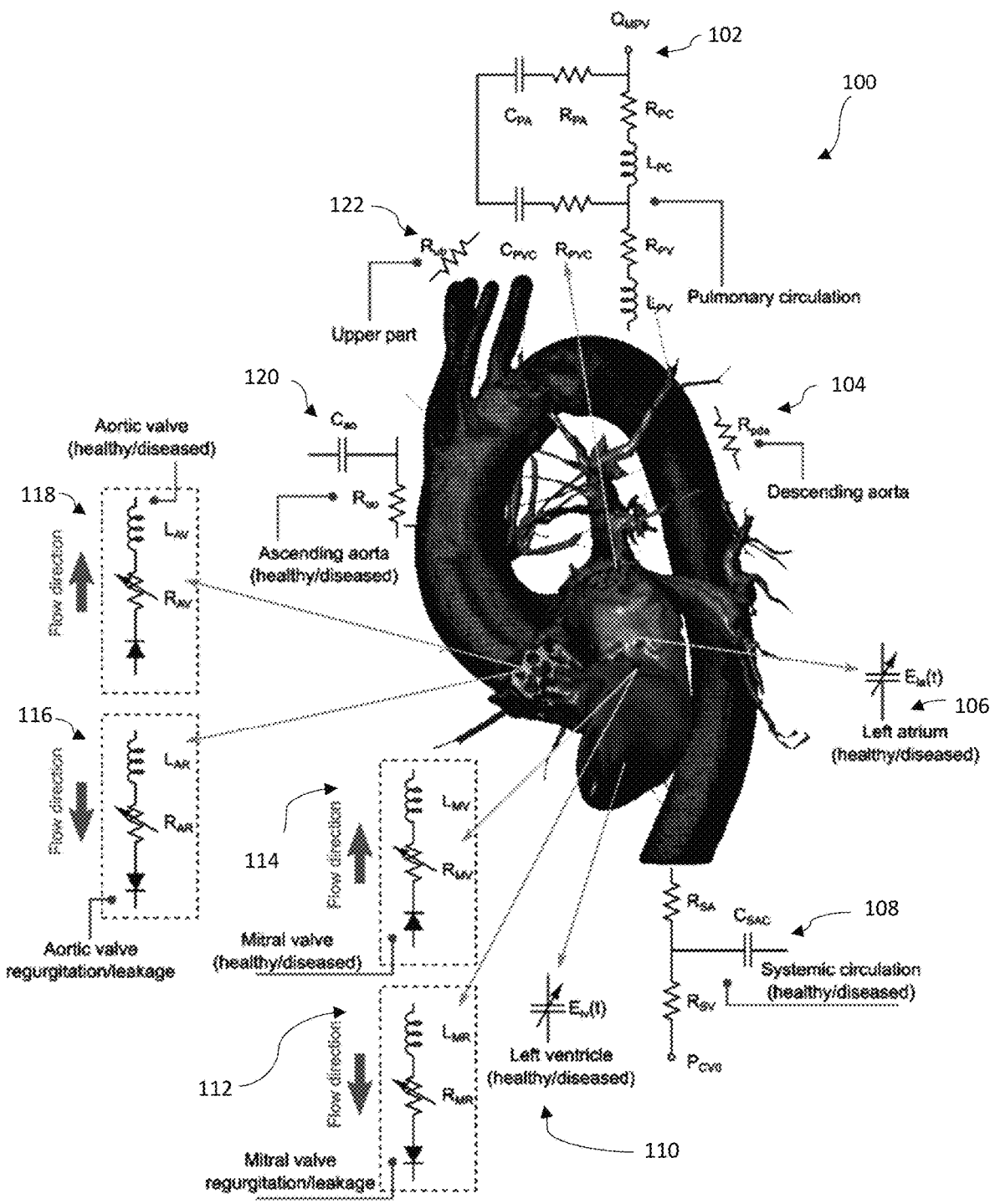
FIG. 1A shows a schematic diagram of the lumped parameter modeling including an anatomical representation, in accordance with one or more embodiments.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is used or present.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers or computing devices may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloads, magnetic and electronic storage media, digital and analog signals, and the like. The computer useable instructions may also be in various forms, including compiled and non-compiled code.

C3VI-CMF and the Lumped Parameter Model

In one embodiment, there is provided a method for determining an indicator of hemodynamic function for a subject comprising providing a lumped parameter model. In one embodiment the lumped parameter model comprises a plurality of sub-models defined by a set of time-varying functions. The time-varying functions may be defined by at least one sub-model parameter. In one embodiment, the method comprises receiving a plurality of input parameters for the subject. For example, the input parameters may comprise at least one input parameter obtained using a non-invasive cardiovascular imaging modality and at least one input parameter indicative of blood pressure. An indicator of hemodynamic function may then be determined for the subject based on at least one sub-model parameter determined for the subject based on the lumped parameter model and the plurality of input parameters.

Referring first to FIG. 1A, there is shown a schematic 100 of a lumped parameter modeling including an anatomical representation of the heart, in accordance with one or more embodiments.

In one embodiment, the C3VI-CMF algorithm comprises a parameter estimation algorithm and a lumped-parameter model that includes several sub-models allowing for the determination of hemodynamic indicators for a subject, such as an indicator associated with any combination of complex valvular, vascular and ventricular diseases in both pre and post intervention conditions.

The model may include a plurality of sub-models, including, for example, sub-models representative of the left atrium 106, left ventricle 110, aortic valve 118, aortic valve regurgitation 116, mitral valve 114, mitral valve regurgitation 112, systemic circulation 108, and pulmonary circulation 102. Abbreviations shown in FIG. 1A are similar as in Table 1.

In one embodiment, the method comprises receiving a plurality of input parameters for the subject. In one embodiment, the input parameters comprise at least one input parameter obtained using a non-invasive cardiovascular imaging modality and at least one input parameter indicative of blood pressure. For example, input parameters may be measured using Doppler echocardiography 152 and sphygmomanometer 162.

In one embodiment, the methods and systems described herein integrate a parameter-estimation algorithm, the lumped-parameter model, non-invasive cardiovascular imaging, such as clinical Doppler echocardiography, and sphygmomanometer measurements to determine a patient-specific in silico model of the cardiovascular system. For example, in one embodiment the following input parameters are determined based on Doppler echocardiography: forward left ventricular outflow tract stroke volume, heart rate, ejection time, ascending aorta area, left ventricular outflow tract area, aortic valve effective orifice area, mitral valve effective orifice area, and grading of aortic and mitral valves regurgitation severity.

Figure 1B:
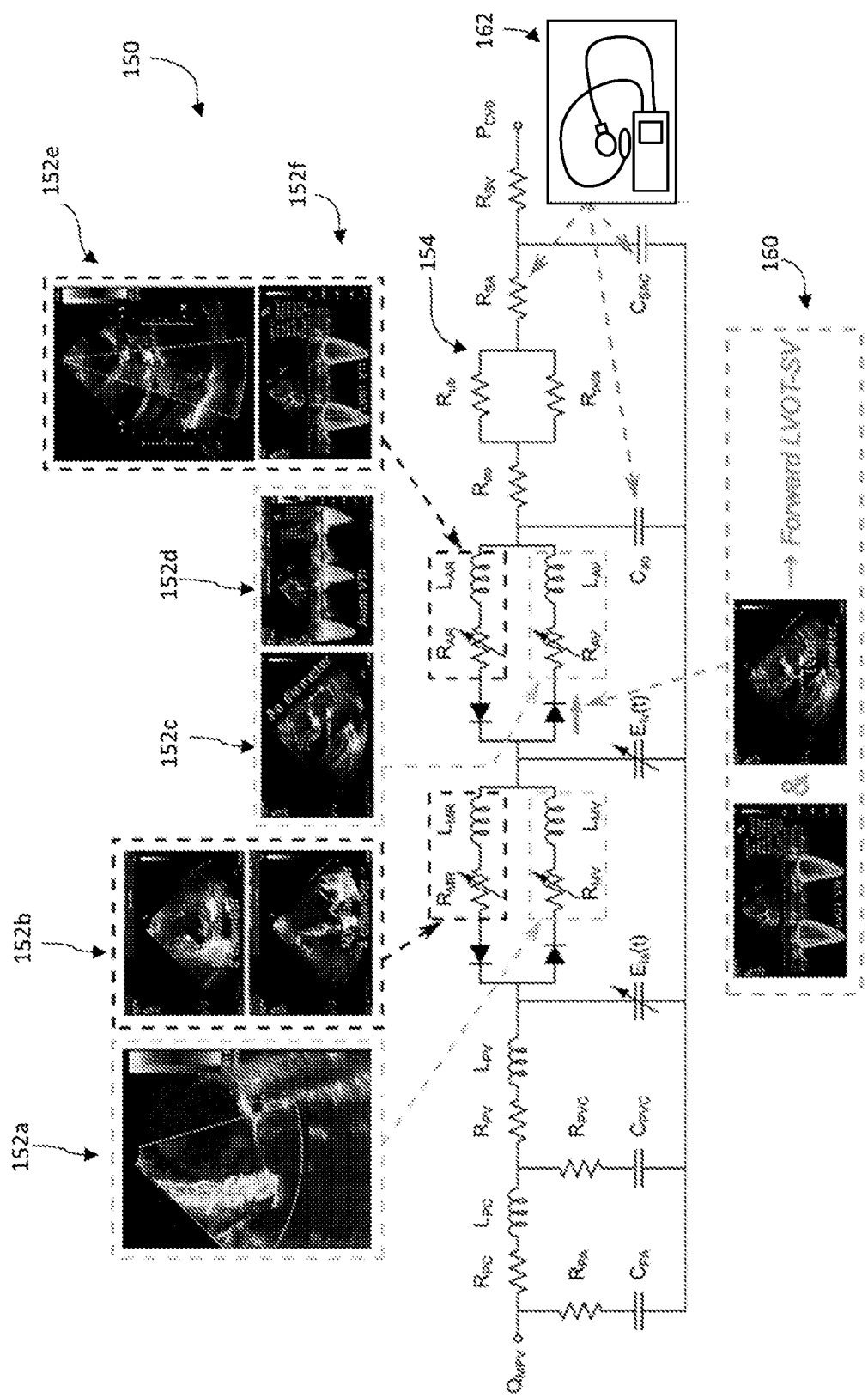
FIG. 1B shows a schematic diagram of the lumped parameter modeling including an electrical representation, in accordance with one or more embodiments.
Figure 2A:
FIGS. 2A, 2B, 2C, 2D and 2E show views of the heart used for Doppler echocardiography measurements, in accordance with one or more embodiments.
Figure 2B:
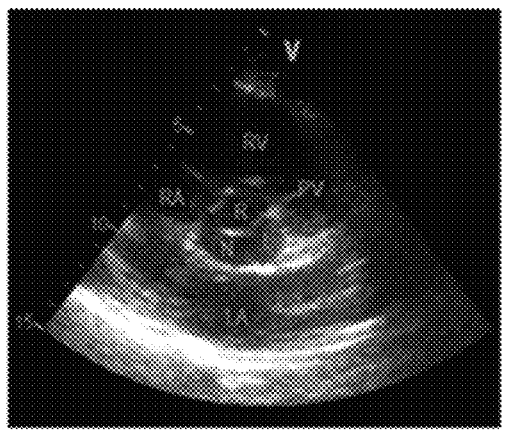
Figure 2C:
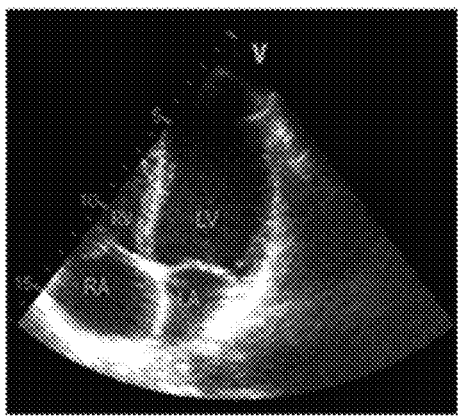
Figure 2D:
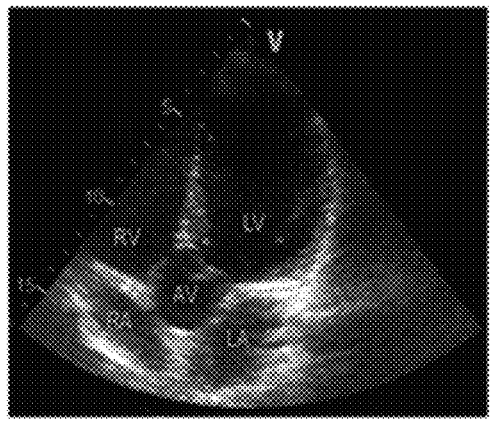
Figure 2E:
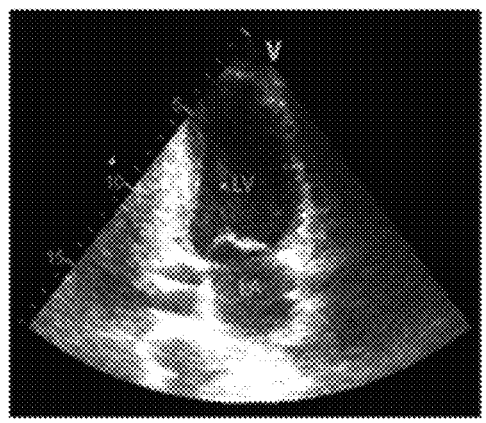

Referring next to FIG. 1B, there is shown a schematic diagram 150 of the lumped parameter modeling including an electrical circuit representation 154 of FIG. 1A, in accordance with one or more embodiments. The schematic diagram 150 shows input parameters in the electrical circuit representation 154 that may be determined based on non-invasive cardiovascular imaging such as by using Doppler echocardiography images 152. The electrical circuit representation 154, including the corresponding electrical component identities, may be used in order to determine the lumped parameter model.

Referring next to FIG. 2, there are shown five views 200, 210, 220, 230, and 240 of a heart collected using Doppler echocardiography, in accordance with one or more embodiments. For FIG. 2, the following abbreviations apply—LVOT: left ventricular outflow tract; AV: aortic valve; LA: left atrium; RV: right ventricle; RA: right atrium; PV: pulmonary valve. A parasternal long axis view 200 of the heart is shown, including blood entering the left ventricle through the left atrium, and exiting through the left ventricular outflow tract leading to the aortic valve. A parasternal short axis view 210 of the heart shows the aortic valve leaflets opening and closing. Above the aortic valve is the right ventricle, through which blood exits the right ventricular outflow tract into the pulmonary artery. An apical four-chamber view 220 of the heart shows the right atrium opening into the right ventricle, and the left atrium opening into the left ventricle. An apical five-chamber view 230 of the heart: mitral valve allows blood to enter the left ventricle, then exit through the aortic valve. An apical two-chamber view 240 of the heart shows blood moving from the left atrium, through the mitral valve, into the left ventricle. These parameters may be measured in the parasternal long axis, parasternal short axis, apical two-chamber, apical four-chamber, and apical five-chamber views of the heart (FIG. 2).

Figure 3A:
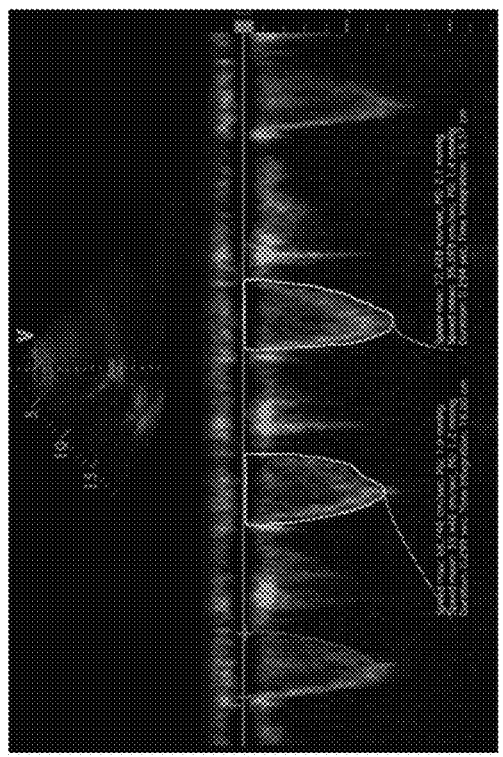
FIGS. 3A, 3B, 3C, and 3D show Doppler echocardiography measurements for left ventricular outflow tract and the aorta in accordance with one or more embodiments, including FIG. 3A showing left ventricular outflow tract diameter, measured in the parasternal long axis view.
Figure 3C:
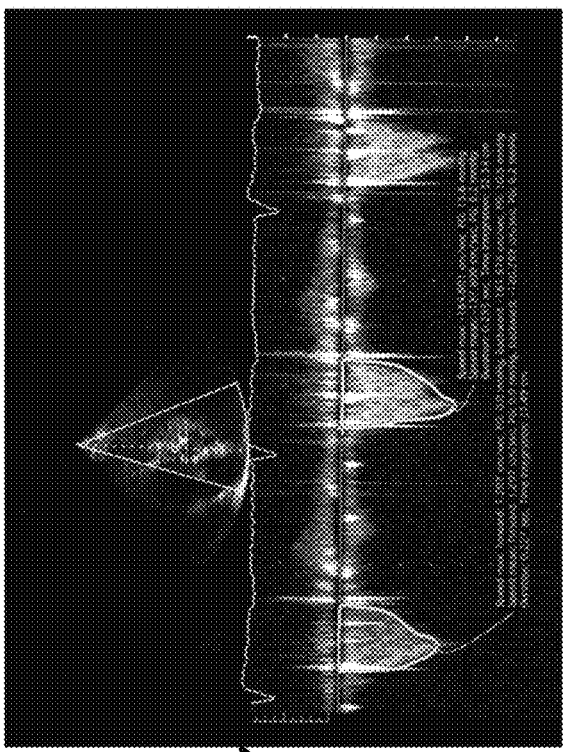
Figure 3B:
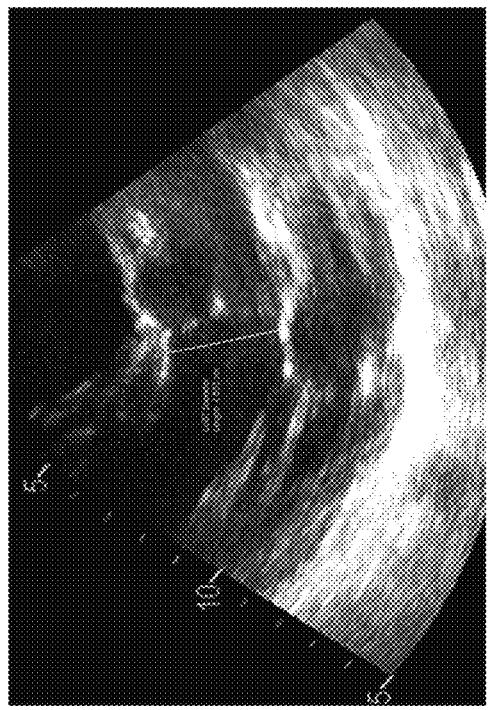
Figure 3D:
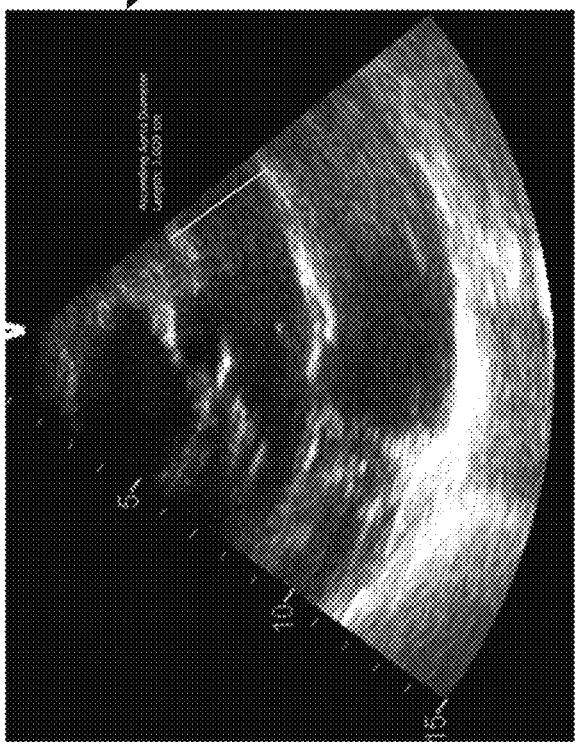

Referring to FIGS. 3A, 3B, 3C, and 3D, there is shown Doppler echocardiography measurements for left ventricular outflow tract and the aorta in accordance with one or more embodiments. FIG. 3A shows the left ventricular outflow tract diameter 300, measured in the parasternal long axis view. FIG. 3B shows the left ventricular outflow tract velocity time integral 310, taken as the average of the areas. FIG. 3C shows an ascending aorta diameter 320, measured in the parasternal long axis view. FIG. 3D shows an aorta velocity time integral 330, taken as the average of the areas.

Other input parameters of the model may include systolic and diastolic blood pressures measured using a suitable device such as a sphygmomanometer. Table 1 provides exemplary input parameters used for the lumped parameter modelling and C3VI-CMF.

In one embodiment, the lumped parameter model comprises a plurality of sub-models, the plurality of sub-models defined by a set of time-varying functions comprising at least one sub-model parameter. An exemplary set of time varying functions for modelling cardiovascular function in a lumped parameter model are provided without limitation below.

Heart-Arterial Model

Left Ventricle

Coupling between LV pressure and volume may be determined through a time varying elastance E(t), a measure of cardiac muscle stiffness.

$$E(t) = \frac{P_{LV}(t)}{V(t) - V_0} \quad (1)$$

where $P_{LV}(t)$, $V(t)$ and $V_0$ are left ventricle time-varying pressure, time-varying volume and unloaded volume, respectively[15]. The amplitude of E(t) may be normalized with respect to maximal elastance $E_{max}$, i.e., the slope of the end-systolic pressure-volume relation, giving $E_N(t_N)=E(t)/E_{max}$. Time may be normalized with respect to the time to reach peak elastance, $T_{Emax}$ ($t_N=t/T_{Emax}$).

$$E_{max}E_N(t_N) = \frac{P_{LV}(t)}{V(t) - V_0} \quad (2)$$

To model the normalized elastance function of the LV, three functions were evaluated: (1) a summation of Gaussian functions[20,21], (2) a Boltzmann Distribution[22], and (3) a double Hill function[23,24]. The lumped parameter model was simulated using these elastance functions for several different patient input parameters and it was determined that the double Hill function model gave the most accurate (physiologically realistic) results for the pressure, flow, and volume waveforms. The use of the double Hill function was motivated by myocyte recruitment during preload, which is fundamentally a cooperative process[25] and consequently, may be modeled by a sigmoidal Hill function[26]. Both the Gaussian function and Boltzmann distribution not only gave sub-par results compared to the Hill model, but also did not model the myocyte recruitment mechanism: The Gaussian function is symmetric about a mean[20], which is not correct for the present model because contraction and relaxation are not symmetric processes[27-36]. The Boltzmann distribution is a probability distribution of physical states[22], and hence does not capture the dynamic cooperativity of myocytes recruitment. Consequently, to model the LV time-varying elastance curves (E), a double Hill function was used as the following[23,24]:

$$E(t) = N \left( \frac{\left(\frac{t}{\tau_1}\right)^{m_1}}{1+\left(\frac{t}{\tau_1}\right)^{m_1}} \right) \left( \frac{1}{1+\left(\frac{t}{\tau_2}\right)^{m_2}} \right) + E_{min} \quad (3)$$

where N, $\tau_1$, $\tau_2$, $m_1$, $m_2$ and $E_{min}$ are elastane normalization, ascending time translation, descending time translation, ascending gradient, descending gradient, and minimum elastance, respectively (see Table 1). A double Hill function may be used to model the contraction and relaxation in the heart chambers: in equation 3, the first term in brackets corresponds to the contraction of the chamber and the second term in brackets corresponds to the relaxation of the chamber. $\tau_1$, $\tau_2$, $m_1$, $m_2$ govern the time translation and gradient of the elastance function respectively. Parameter values used for the elastance function were adapted from[27-36] to obtain physiologically realistic waveforms for pressure, volume, and flow that can be found in Table 1. While Table 1 provides exemplary parameter values, the skilled person will appreciate that they may be adjusted accordingly to reflect physiological realistic values for the embodiments described herein.

Left Atrium

Coupling between LA pressure and volume may be performed through a time varying elastance E(t), a measure of cardiac muscle stiffness, using the same procedure as outlined above for the LV. The elastance function used for the LA may be as defined in equations 2 and 3[23,24]; parameter values used can be found in Table 1. Additionally, to take into account the relative onset of contraction for the LA and LV, a phase lag may be used in the LA elastance function[23]. Specifically, LV contraction was initiated at T=0, and LA contraction was initiated at 0.85 T[23], resulting in a time delay of 0.15 T.

Modeling Heart Valves
Modeling Aortic Valve

Aortic valve. The aortic valve may be modeled using the net pressure gradient formulation ($PG_{net}$) across the aortic valve during LV ejection. This formulation may express the instantaneous net pressure gradient across the aortic valve (after pressure recovery) as a function of the instantaneous flow rate and the energy loss coefficient and links the LV pressure to the ascending aorta pressure:

$$PG_{net}|_{AV} = \frac{2\pi\rho}{\sqrt{E_L Col|_{AV}}} \frac{\partial Q(t)}{\partial t} + \frac{\rho}{2E_L Col_{AV}^2} Q^2(t) \quad (4)$$

and $$E_L Col|_{AV} = \frac{(EOA|_{AV})A_{AO}}{A - EOA|_{AV}} \quad (5)$$

where $E_L Col|_{AV}$, $EOA|_{AV}$, $A_{AO}$, $\rho$ and Q are the valvular energy loss coefficient, the effective orifice area, ascending aorta cross sectional area, fluid density and transvalvular flow rate, respectively. $E_L Col|_{AV}$, representing the 'recovered EOA', may denote valve effective orifice area adjusted for the area of the aorta at the level of sinotubular junction.

Aortic regurgitation. Aortic regurgitation (AR) may be modeled using the same analytical formulation as aortic stenosis. AR pressure gradient is the difference between aortic pressure and LV pressure during diastole.

$$PG_{net}|_{AR} = \frac{2\pi\rho}{\sqrt{E_L Col|_{AR}}} \frac{\partial Q(t)}{\partial t} + \frac{\rho}{2E_L Col_{AR}^2} Q^2(t) \quad (6A)$$

and $$E_L Col|_{AR} = \frac{EOA_{AR} A_{LVOT}}{A_{LVOT} - EOA_{AR}} \quad (6B)$$

where $E_L Col|_{AR}$, $EOA_{AR}$ and $A_{LVOT}$ are regurgitation energy loss coefficient, regurgitant effective orifice area and LVOT area, respectively.

Modeling Mitral Valve

Mitral valve. Mitral valve (MV) may be modeled using the analytical formulation for the net pressure gradient ($PG_{net}|_{MV}$) across the MV during LA ejection. This formulation expresses the instantaneous net pressure gradient across the LA and vena contracta as an unsteady incompressible inviscid flow, where viscous effect is ignored, with a constant density. $PG_{net}|_{MV}$ expresses as a function of $\rho$, $Q_{MV}$, $EOA_{MV}$ and $M_{MV}$ where these quantities may represent the density of fluid, transvalvular flow rate, effective orifice area and inertance, respectively. In this formulation, the pressure recovery phenomenon may be ignored because the effect is negligible due to the large volume of the LV[37].

$$PG_{net}|_{AR} = \frac{M_{MV}}{EOA_{M_V}} \frac{\partial Q_{MV}(t)}{\partial t} + \frac{\rho}{2EOA_{MV}^2} Q_{MV}^2(t) \quad (7)$$

Mitral regurgitation. Mitral regurgitation (MR) may be modeled using equation 8. MR pressure gradient is the difference between mitral pressure and LA pressure during systole.

$$PG_{net}|_{MR} = \frac{M_{MV}}{EOA_{MR}} \frac{\partial Q(t)}{\partial t} + \frac{\rho}{2EOA|_{MR}^2} Q^2(t) \quad (8)$$

where $EOA|_{MR}$ is MR effective orifice area.

Pulmonary Flow

The pulmonary valve flow waveform may be simulated by a rectified sine curve with duration $t_{ee}$ and amplitude $Q_{MPV}$ as the following.

$$Q_{PV}(t) = Q_{MPV} \sin\left(\frac{\pi t}{t_{ee}}\right), \quad (9)$$

$$t \le t_{ee}; Q_{PV}(t) = 0,$$

$$t_{ee} < t \le T$$

where $Q_{MPV}$, $t_{ee}$ and T are mean flow rate of the pulmonary valve, end-ejection time and cardiac cycle time period, respectively. In this study, Forward LVOT-SV may be the only input flow condition which is reliable to measure using DE. $Q_{MPV}$, the mean flow rate of the pulmonary valve, was optimized so that the lump-parameter model could reproduce the desirable DE-measured Forward LVOT-SV.

Determining Arterial Compliance and Peripheral Resistance

The total systemic resistance may be computed as the quotient of the average brachial pressure and the cardiac output (assuming a negligible peripheral venous pressure (mean ~5 mmHg) compared to aortic pressure (mean ~100 mmHg). This total systemic resistance represents the electrical equivalent resistance for all resistances in the current lumped parameter model. Because what the left ventricle faces is the total systemic resistance and not the individual resistances, for the sake of simplicity the aortic resistance, $R_{ao}$, and systemic vein resistance, $R_{SV}$, may be considered as constants and adjust the systemic artery resistance, $R_{SA}$, according to the obtained total systemic resistance. Systemic artery resistance may be evaluated using an optimization scheme outlined in the patient-specific parameter estimation section.

Physiologically, arterial hypertension is determined by two factors: the degree of reduction in the caliber of small arteries or arterioles with an ensuing increase in systemic vascular resistance and mean blood pressure, and the extent of reduction in the arterial compliance with a resulting increase in pulse pressure (systolic minus diastolic blood pressure). For each degree of hypertension, a predicted pulse pressure may be fit to the actual pulse pressure (known by arm cuff sphygmomanometer) obtained from clinical study by adjusting compliances (aorta ($C_{ao}$) and systemic ($C_{SAC}$)). Therefore, for each degree of arterial hypertension, the compliance may be evaluated using an optimization scheme outlined in the patient-specific parameter estimation section.

Patient-Specific Parameter Estimation

The lumped-parameter model may receive patient-specific parameters as its inputs: forward left ventricular outflow tract stroke volume (Forward LVOT-SV), cardiac cycle time (T), ejection time ($T_{EJ}$), $EOA_{AV}$, $EOA_{MV}$, $A_{AO}$, $A_{LVOT}$, $EOA_{AR}$, $EOA_{MR}$ and brachial systolic and diastolic pressures measured by a sphygmomanometer or other suitable device. The following procedure was used to set up the patient-specific lumped-parameter model in the following sequence:

1) Flow Inputs

The lumped-parameter model may use one reliably measured flow parameter as an input: forward left-ventricular outflow tract stroke volume (Forward LVOT-SV) (Equation 10). Forward LVOT-SV is defined as the volume of blood that passes through the LVOT cross sectional area every time the heart beats.

$$\text{Forward } LVOT\text{-}SV = A_{LVOT} \times VTI_{LVOT} = \frac{\pi \times (D_{LVOT})^2}{4} \times VTI_{LVOT} \quad (10)$$

where $D_{LVOT}$, $A_{LVOT}$, and $VTI_{LVOT}$ are LVOT diameter, LVOT area, and LVOT velocity-time integral, respectively, which may be reliably measured using Doppler echocardiography (see FIGS. 3A and 3B).

2) Time Inputs

Cardiac cycle time (T) and ejection time ($T_{EJ}$) may be measured using Doppler echocardiography or another suitable cardiovascular imaging modality.

3) Aortic Valve Inputs:

$A_{AO}$ and $EOA|_{AV}$ were calculated using Equations 11 and 12, respectively.

$$A_{AO} = \frac{\pi \times (D_{AO})^2}{4} \quad (11)$$

$$EOA|_{AV} = \frac{\text{Forward } LVOT\text{-}SV}{VTI_{AO}} \quad (12)$$

where $D_{AO}$ and $VTI_{AO}$ are the diameter of the ascending aorta and velocity time integral in the ascending aorta, respectively (see FIGS. 3C and 3D). $VTI_{AO}$ is the amount of the blood flow going through the aorta which was obtained by tracing the aorta pulse wave flow Doppler envelope. To model the blood flow in the forward direction, $A_{AO}$ and $EOA|_{AV}$ may be substituted into Equation (4) and the constant inductance $$\left(\frac{2\pi\rho}{\sqrt{E_L Col|_{AV}}}\right)$$

and variable resistance $$\left(\frac{\rho}{2E_L Col_{AV}^2} Q(t)\right)$$

parameters may be calculated.

Figure 4A:
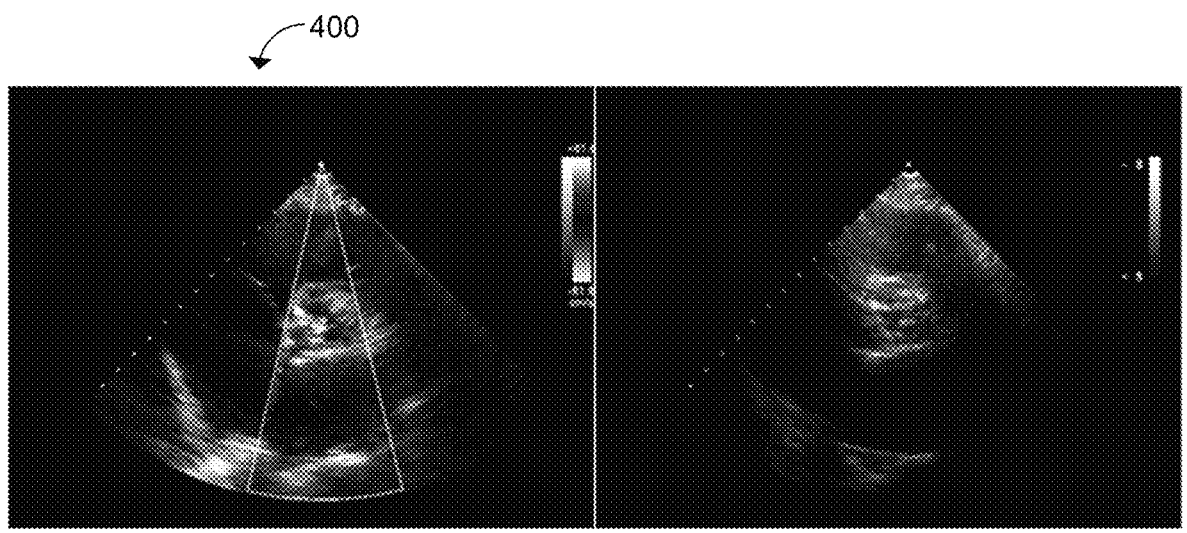
FIGS. 4A, and 4B show Doppler echocardiography investigation for aortic valve regurgitation, in accordance with one or more embodiments.
Figure 4B:
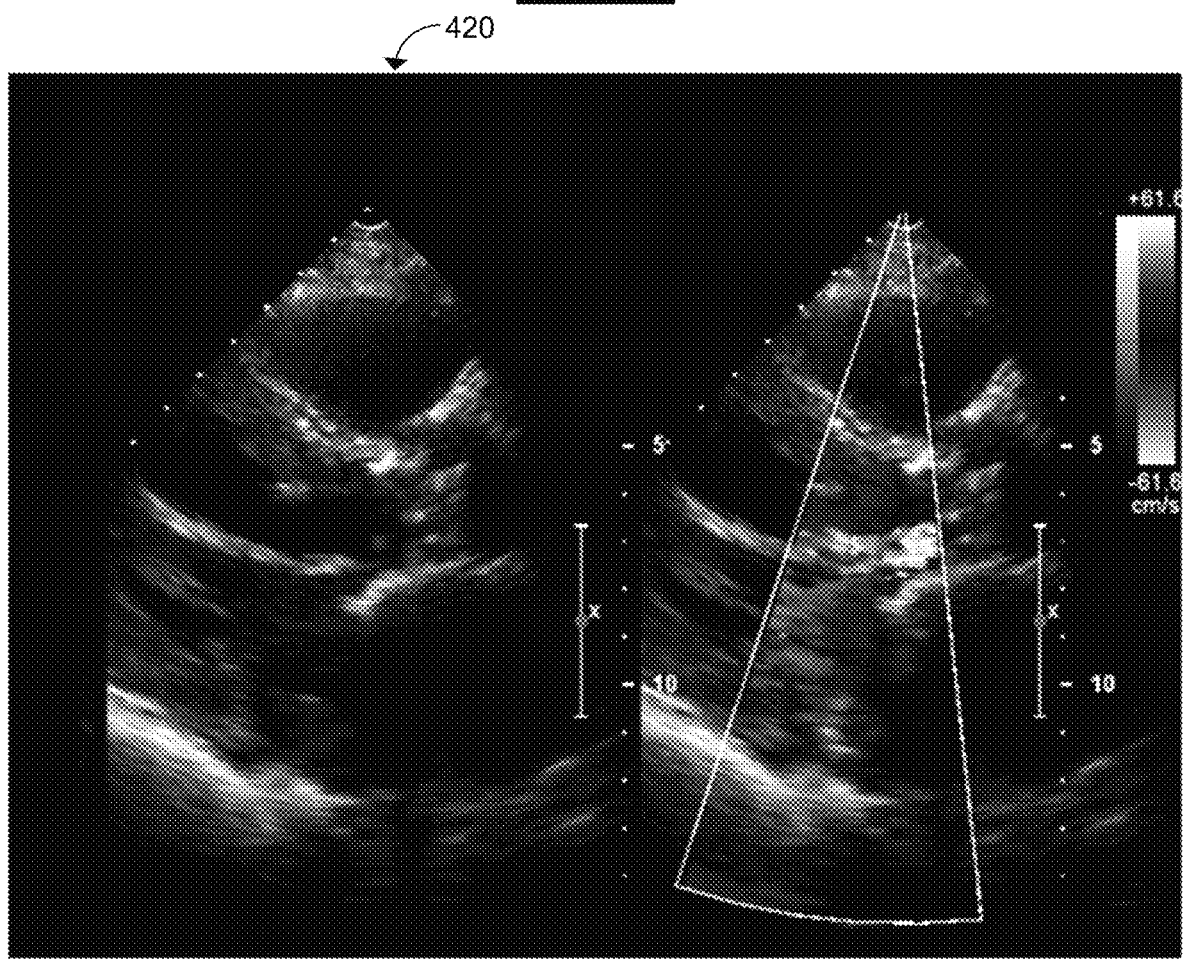

4) Aortic Regurgitation Inputs:

Referring to FIGS. 4A, and 4B, there is shown a Doppler echocardiography investigation for aortic valve regurgitation, in accordance with one or more embodiments. FIGS. 4A, and 4B may be for a subject with Moderate aortic valve regurgitation (0.1 mm² < $EOA_{AR}$ < 0.3 mm²). FIG. 4A shows a parasternal short axis view. FIG. 4B shows a parasternal long axis view.

To evaluate aortic valve regurgitation severity, aortic valve color Doppler images may be used in both long axis, and short axis views. This image may be an example of moderate to severe aortic valve regurgitation in a patient with AS who received TAVR (0.2 mm² < $EOA_{AR}$ < 0.3 mm²).

To model blood flow in the reverse direction (aortic valve insufficiency), $EOA_{AR}$ and $A_{LVOT}$ were substituted into Equation (6) to calculate the variable resistance $$\left(\frac{\rho}{2E_L Col_{AR}^2} Q(t)\right)$$

and constant inductance $$\left(\frac{2\pi\rho}{\sqrt{E_L Col_{AR}}}\right)$$

parameters. For patients with no insufficiency, the reverse branch is not included. $A_{LVOT}$ was quantified using Doppler echocardiography measurements (See e.g. FIGS. 4A and 4B). The $EOA_{AR}$ may be calculated by dividing the regurgitant volume by the time-velocity integral of regurgitant flow using continuous wave Doppler. However, such a calculation may not always yield a correct $EOA_{AR}$ and therefore may not be reliable. Therefore, to quantify Doppler aortic regurgitant effective orifice area ($EOA_{AR}$), aortic valve regurgitation may be investigated using color Doppler images in both the long axis and short axis views by experienced cardiologists and graded qualitatively as either mild regurgitation (equivalent to $EOA_{AR}<0.1$ mm$^2$), mild to moderate regurgitation (equivalent to 0.1 mm$^2<EOA_{AR}<0.2$ mm$^2$), moderate to severe regurgitation (equivalent to 0.2 mm$^2<EOA_{AR}<0.3$ mm$^2$), or severe regurgitation (equivalent to $EOA_{AR}>0.3$ mm$^2$) (see FIGS. 4A and 4B for examples of moderate to severe aortic valve regurgitation in a patient with AS who received TAVR).[38,39]

Figures 5A, 5B:
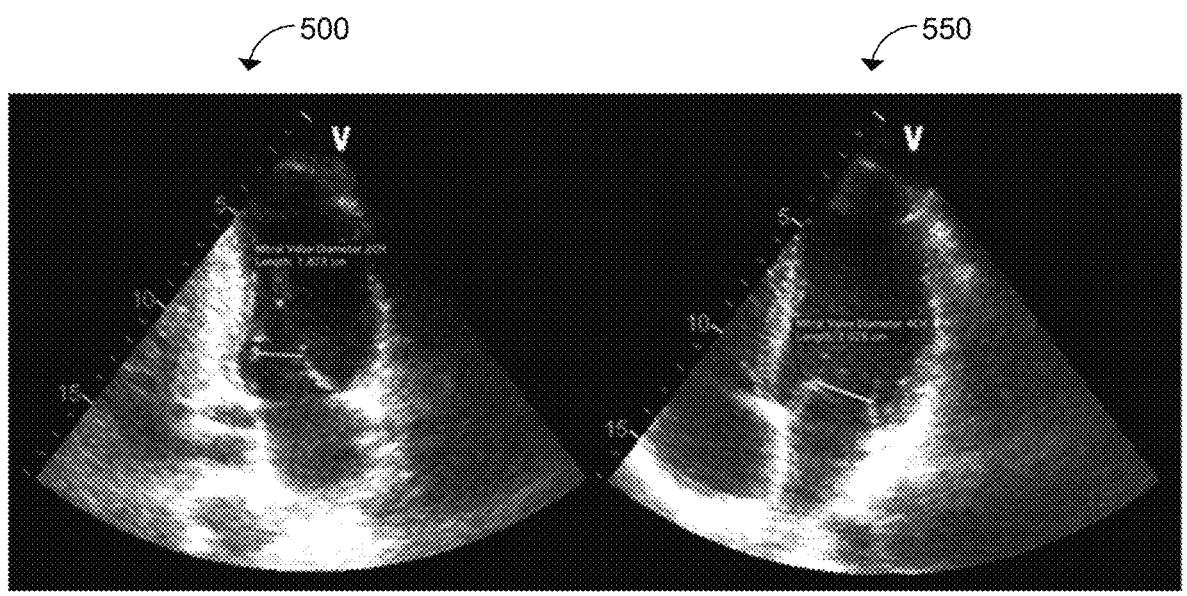
FIGS. 5A and 5B show Mitral valve dimensions, in accordance with one or more embodiments.

5) Mitral Valve Inputs:

Referring to FIGS. 5A and 5B, there are shown Mitral valve dimensions. FIG. 5A shows Mitral valve diameter ($d_1$), measured in apical two-chamber view; FIG. 5B shows Mitral Valve diameter ($d_2$), measured in apical four-chamber view. Mitral valve is an ellipse and its area is quantified using $$A_{MV} = \frac{\pi * d_1 * d_2}{4}.$$

To model the blood flow in the forward direction, mitral valve area was substituted into Equation (8) and the constant inductance $$\left(\frac{M_{MV}}{EOA_{M_V}}\right)$$

and variable resistance $$\left(\frac{\rho}{2EOA|_{MV}^2} Q_{MV}(t)\right)$$

parameters were calculated. Mitral valve is approximately an ellipse and its area was quantified using $$A_{MV} = \frac{\pi * d_1 * d_2}{4}$$

where $d_1$ and $d_2$ are mitral-valve diameters measured in the apical two-chamber and apical four-chamber views, respectively.

Figure 6A:
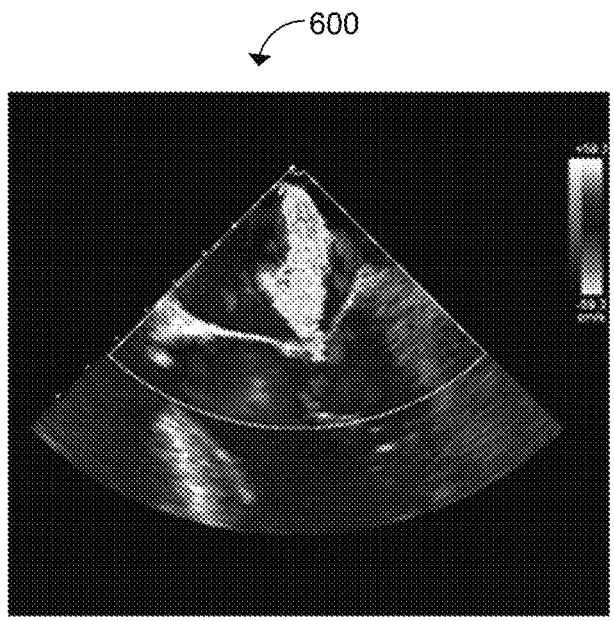
FIGS. 6A, 6B, and 6C show Doppler echocardiography investigation for mitral valve regurgitation, in accordance with one or more embodiments.
Figure 6B:
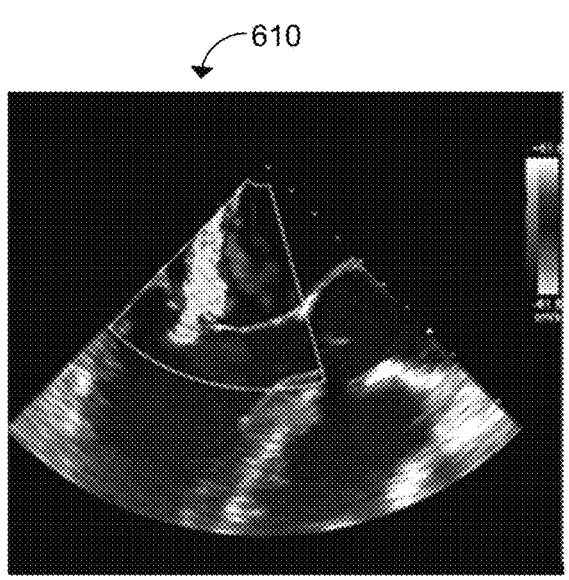
Figure 6C:
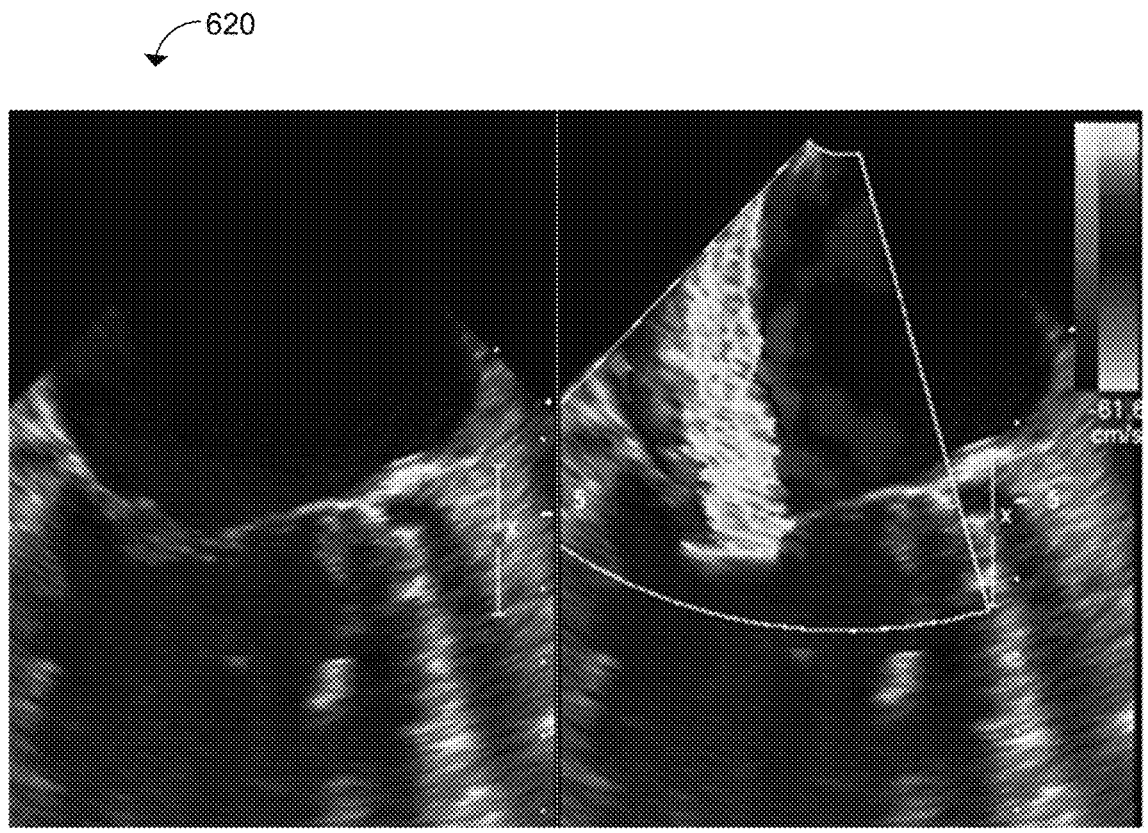

6) Mitral Regurgitation Inputs:

Referring to FIGS. 6A, 6B, and 6C there is shown a Doppler echocardiography investigation for mitral valve regurgitation, in accordance with one or more embodiments.

To evaluate mitral valve regurgitation severity, mitral valve color Doppler images may be used in apical four-chamber view (FIG. 6A), parasternal long axis view (FIG. 6B), and apical two-chamber view (FIG. 6C). The three images shown in FIGS. 6A, 6B, and 6C are of the same patient, and each demonstrates severe mitral valve regurgitation. These figures are examples of severe mitral valve regurgitation in a patient with AS who received TAVR (0.2 mm$^2<EOA_{MR}>0.3$ mm$^2$).

To model blood flow in the reverse direction (mitral-valve insufficiency), $EOA_{MR}$ may be substituted into Equation (9) to calculate the variable resistance $$\left(\frac{\rho}{2EOA|_{MR}^2} Q(t)\right)$$

and constant inductance $$\left(\frac{M_{MV}}{EOA_{MR}}\right)$$

parameters. For patients with no insufficiency, the reverse branch may not be included. As described for the aortic-valve regurgitation, calculation of the regurgitant effective orifice area by dividing the regurgitant volume by the time-velocity integral of regurgitant flow using continuous wave Doppler may not be reliable. Therefore to quantify mitral regurgitant effective orifice area ($EOA_{MR}$), mitral valve regurgitation may be investigated using color Doppler images in the apical four-chamber, parasternal long axis, and apical two-chamber views by experienced cardiologists and graded qualitatively as either mild regurgitation (equivalent to $EOA_{MR}<0.1$ mm$^2$), mild to moderate regurgitation (equivalent to 0.1 mm$^2<EOA_{MR}<0.2$ mm$^2$), moderate to severe regurgitation (equivalent to 0.2 mm$^2<EOA_{MR}<0.3$ mm$^2$), or severe regurgitation (equivalent to $EOA_{MR}>0.3$ mm$^2$) (see FIGS. 6A, 6B, and 6C for examples of severe mitral-valve regurgitation in a patient who received TAVR).

7) End Systolic Volume and End Diastolic Volume

Figure 7A:
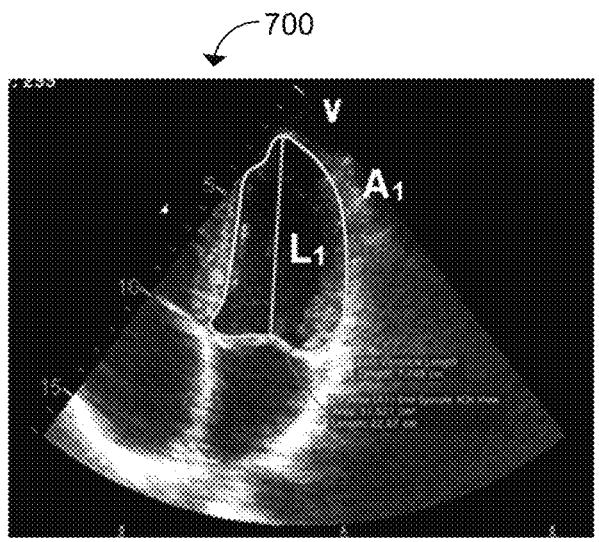
FIGS. 7A, 7B, 7C, and 7D show LV volumes, in accordance with one or more embodiments.
Figure 7B:
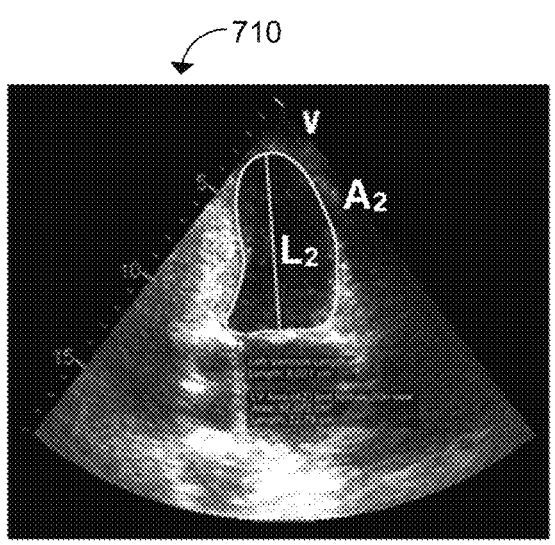
Figure 7C:
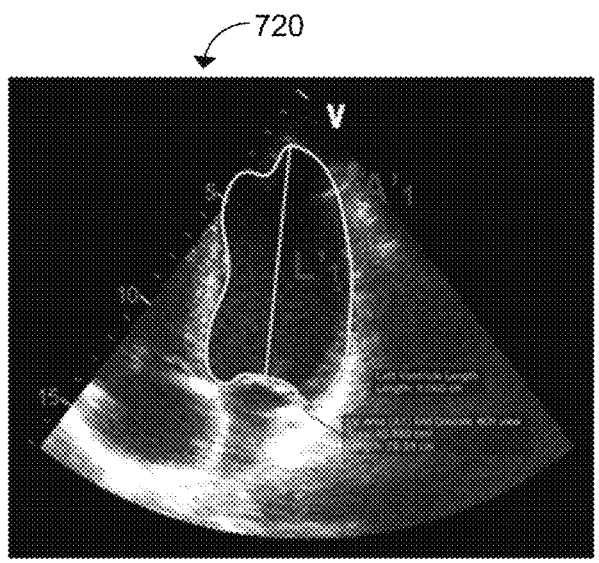
Figure 7D:
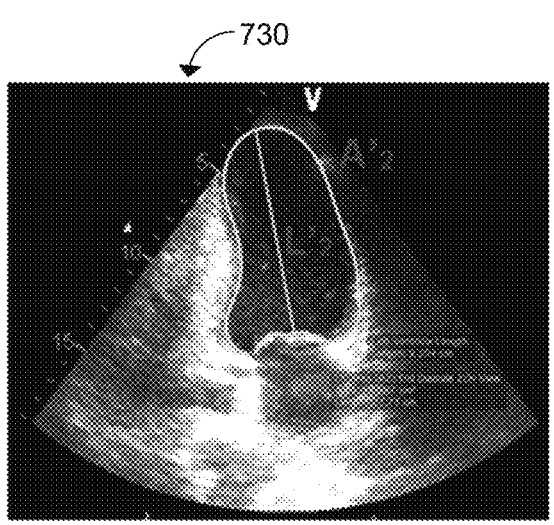

Referring to FIGS. 7A, 7B, 7C, and 7D there are shown LV volumes, in accordance with one or more embodiments. FIGS. 7A and 7B show an end of systole LV volume in apical four-chamber view and apical two chamber view respectively. FIGS. 7C and 7D show an end of diastole LV volume in apical four-chamber view and apical two-chamber view respectively.

End systolic volume (ESV) or end diastolic volume (EDV) measured using Doppler echocardiography may be input into the lumped-parameter model to adjust starting and ending volumes in the P-V loop diagram. For this purpose, the Biplane Ellipsoid model may be used to calculate the instantaneous LV volume at the end of diastole and the end of systole using the following Equation.

$$V = \frac{A_1 * A_2}{AVG(L_1 \& L_2)} \quad (13)$$

where $A_1$, $A_2$, $L_1$, $L_2$ and AVG ($L_1\&L_2$) are LV area measured in the apical four-chamber view, LV area measured in the apical two-chamber view, LV length measured in the apical four-chamber view, LV length measured in the apical two-chamber view, and average of these two LV lengths, respectively (Refer to FIGS. 7A, 7B, 7C, and 7D for examples).

Ejection Fraction may be Calculated as Follows:

$$EF = \frac{EDV - ESV}{EDV} \quad (14)$$

8) Left-Ventricle Inputs

The cardiac cycle time (T) may be substituted into $\tau_1$, $\tau_2$, $m_1$ and $m_2$ in Table 1 and then those values may be substituted into Equation 3 to determine the elastance function.

9) Left-Atrium Inputs

The cardiac cycle time (T) may be substituted into $\tau_1$, $\tau_2$, $m_1$ and $m_2$ in Table 1 and then those values may be substituted into Equation 3 to determine the elastance function.

10) Parameter Estimation for Systemic Circulation:

Parameters $R_{SA}$, $C_{SAC}$, and $C_{ao}$ may be optimized so that the aorta pressure calculated using the model matches the patient's systolic and diastolic brachial pressures measured using a sphygmomanometer (see computational algorithm section for details). The initial values of these parameters are given in Table 1.

Computational Algorithm

Figure 8:
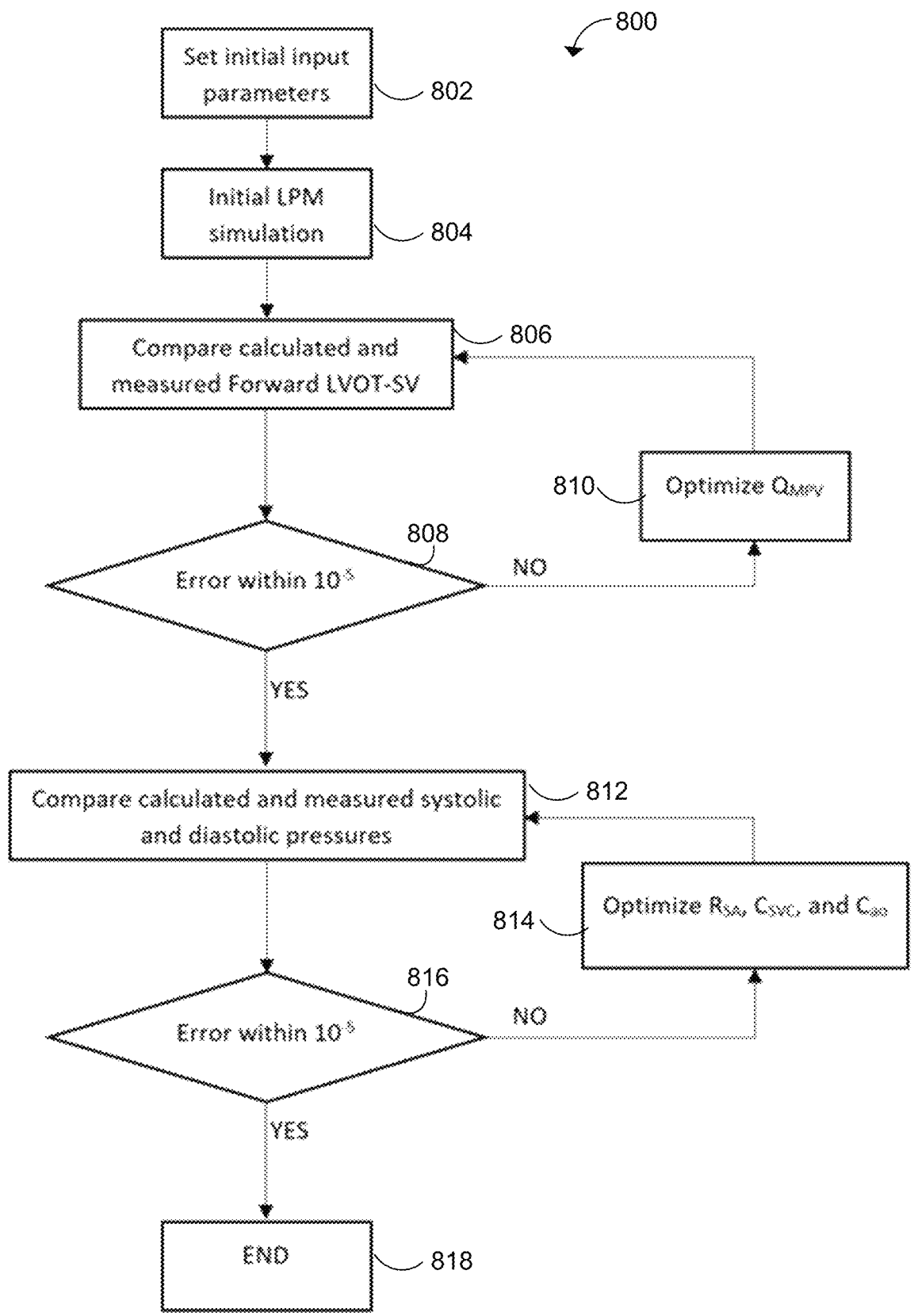
FIG. 8 shows a patient-specific response optimization method, in accordance with one or more embodiments.

FIG. 8 shows one embodiment of a process for optimizing a lumped parameter model in accordance with the present disclosure. The lumped-parameter model may be numerically analyzed by creating and solving a system of ordinary differential equations, for example in Matlab Simscape™ (MathWorks, Inc.). These differential equations may be enhanced by adding additional functions written in Matlab and Simscape. Matlab's ode23t trapezoidal rule variable-step solver may be used to solve the system of differential equations with an initial time step of 0.1 milliseconds. At 802, the convergence residual criterion may be set to $10^{-6}$ $^{and}$ initial voltages and currents of capacitors and inductors may be set to zero. At 804, the model may be run for several cycles to reach steady state before starting the response optimization process described below.

A double Hill function representation of a normalized elastance curve for human adults[23,24] may be used to generate a signal to model LV elastance. It was shown that this elastance formulation may correctly represent the LV function independent from its healthy and/or pathological condition. Simulations may start at the onset of isovolumic contraction. The instantaneous LV volume, V(t), may be calculated using the LV pressure, $P_{LV}$, and the time varying elastance (Equation 1). The LV flow rate may be subsequently calculated as the time derivative of the instantaneous LV volume. The same approach may be used to obtain the left-atrium volume, pressure and flow rate. PLV may be first calculated using the initial values of the model input parameters from Table 1. The Forward LVOT-SV calculated using the lumped-parameter model may be fitted to the one measured (Equation 10) by optimizing $Q_{MPV}$ (as detailed below). Finally, for each patient $R_{SA}$, $C_{SAC}$, and $C_{ao}$ may be optimized to fit the aorta pressure from the model to the patient systolic and diastolic pressures measured using a sphygmomanometer.

In order to correctly simulate the conditions of the body of each patient, some of the parameters of the model may be optimized so that the lumped-parameter model reproduces the physiological measurements performed in the patient. An extensive parameter sensitivity analysis was conducted. It was found using such a sensitivity analysis the negligible effect of changes in the pulmonary parameters (e.g., $C_{PVC}$) on the model output variables. These pulmonary parameters are therefore not included in the parameter-identification process and the values given in Table 1 were used.

Simulink Design Optimization toolbox may be used to optimize the response of the lumped-parameter model using the trust region reflective algorithm implemented in the Matlab fmincon function. The response optimization may be performed in two sequential steps with tolerances of $10^{-6}$ (FIG. 8). At 806, the error between the Forward LVOT-SV calculated by the lumped-parameter model and the one measured in each patient is determined. At 808, once the error between the Forward LVOT-SV calculated by the lumped-parameter model and the one measured in each patient is below an error threshold (for example, $10^{-5}$), the method may proceed to the second step. At 810, in the first step $Q_{MPV}$, the mean flow rate of the pulmonary valve may be optimized to minimize the error between the Forward LVOT-SV calculated by the lumped-parameter model and the one measured in each patient and the method continues at 806.

At 812 the systolic and diastolic pressures determined from the lumped parameter model are compared. At 816, if the error between the two is below an error threshold (for example, $10^{-5}$), the method may be completed. In the second step of the optimization, $R_{SA}$, $C_{SAC}$, and $C_{ao}$ may be optimized at 814 so that maximum and minimum of the aorta pressure were respectively equal to the systolic and diastolic pressures measured using a sphygmomanometer in each patient.

C3VI-CMF Provides Quantifiable Hemodynamic Indicators of Cardiovascular Function The sophisticated vascular network connected to the heart, impose boundary conditions on it. As the local flow dynamics are influenced by downstream and upstream conditions, replicating correct flow and pressure conditions is critical for determining indicators of hemodynamic function and developing a patient-specific cardiovascular simulator. This not only gives patient-specific flow and pressure conditions to the local flow but also enables investigation of the effects of local hemodynamics on the global circulatory physiology. Investigating the details of flow and pressures in the presence of C3VI is very challenging because of the interactions between disease constituents and amplifying adverse effects of one another. Although cardiac catheterization is the gold standard for evaluating pressure and flow through the heart and circulatory system in clinics, it is invasive, expensive, and high risk and therefore not practical for diagnosis in routine daily clinical practice or serial follow-up examinations. Most importantly, cardiac catheterization only provides access to the blood pressure in very limited regions rather than details of the physiological pulsatile flow and pressures throughout the heart and the circulatory system.

Notably as demonstrated in Example 1 and shown in FIGS. 9 and 10, use of the patient-specific C3VI-CMF lumped parameter model described herein was validated against gold-standard cardiac catheterization data and shown to accurately predict beat-to-beat pressure waveforms and peak pressures.

In some embodiments, C3VI-CMF may also provide other hemodynamic indicators such as details of the physiological pulsatile flow and pressures throughout the heart and the circulatory system, including in subjects with C3VI. For example, it may provide instantaneous quantities including, but not limited to, left-ventricle pressure, aorta pressure, mitral and left-ventricle flow, left ventricle and left atrium volumes, etc. For example, FIGS. 11 to 13 show samples of C3VI-CMF calculations for the same C3VI patients (Patients #1, #2 and #3) whose catheter and C3VI-CMF data for validation are shown (FIGS. 9A(i) 9A(ii), 9B(i), 9B(ii), 9C(i), and 9C(ii)). Use of the C3VI-CMF lumped parameter model was able to predict and quantify changes in various hemodynamic indicators including heart workload pre and post intervention. As shown in FIG. 14, the embodiments described herein allow for the determination of the relative contributions of one or more C3VI disease constituents, such as mitral valve regurgitation or aortic valve stenosis, to cardiovascular disease in a subject. This information may then be used for diagnosing, monitoring or prognosing cardiovascular disease or to select specific interventions for the treatment of cardiovascular disease.

Implementation

In one or more embodiments, C3VI-CMF as described herein may be implemented without imitation as: (1) a personal wearable device or as a mobile application for patient monitoring; (2) a module incorporated in the software of Doppler echocardiography machines for diagnosis and prediction; and (3) a monitoring and diagnostic device for ambulatory care and intensive and critical care unit.

Figure 15:
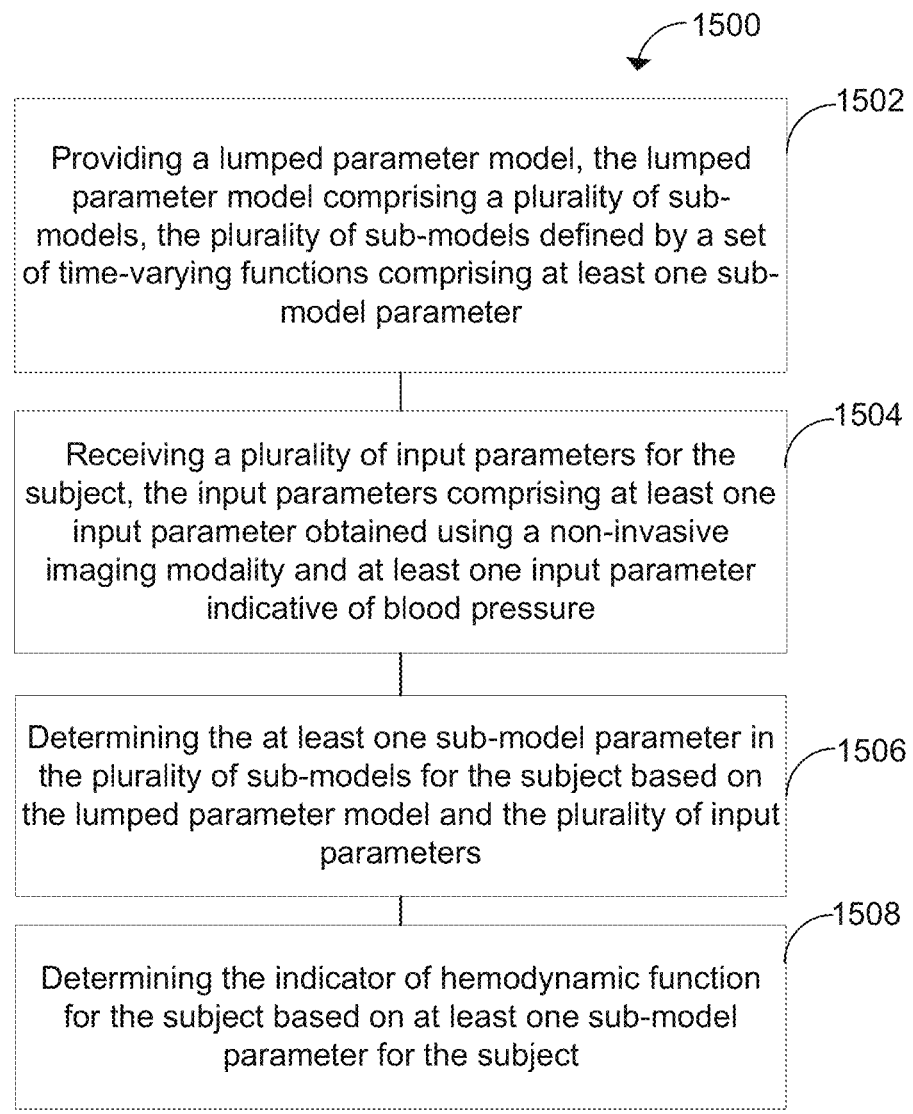
FIG. 15 shows a non-invasive method for determining an indicator of hemodynamic function for a subject in accordance with one or more embodiments.

Referring next to FIG. 15, there is a method diagram 1500 showing a non-invasive method for determining an indicator of hemodynamic function for a subject in accordance with one or more embodiments.

At 1502, the method comprises providing a lumped parameter model, the lumped parameter model comprising a plurality of sub-models, the plurality of sub-models defined by a set of time-varying functions comprising at least one sub-model parameter. As described herein, the lumped parameter model models cardiovascular function by modelling blood fluid dynamics, e.g., flow and pressure as a function of time within the heart and circulatory system.

At 1504, the method comprises receiving a plurality of input parameters for the subject, the input parameters comprising at least one input parameter obtained using a non-invasive imaging modality and at least one input parameter indicative of blood pressure. In one embodiment, the input parameters are obtained using Doppler echocardiography and a sphygmomanometer or other suitable device. In one embodiment, the input parameters comprise one or more cardiovascular anatomical measurements. Patient-specific input parameters may include forward left ventricular outflow tract stroke volume (Forward LVOT-SV), cardiac cycle time (T), ejection time ($T_{EJ}$), $EOA_{AV}$, $EOA_{MV}$, $A_{AO}$, $A_{LVOT}$, $EOA_{AR}$, $EOA_{MR}$ as described herein and determined based on Doppler echocardiography imaging data.

In one embodiment, the input parameters indicative of blood pressure comprise a diastolic blood pressure and a systolic blood pressure for the subject.

At 1506, the method comprises determining at least one sub-model parameter in the plurality of sub-models for the subject based on the lumped parameter model and the plurality of input parameters. For example, in one embodiment the method comprises determining at least one sub-model parameter by solving a system of differential equations based on the time-varying functions using a computer processor.

At 1508, the method comprises determining the indicator of hemodynamic function for the subject based on at least one sub-model parameter for the subject. In some embodiments, the indicator of hemodynamic function is the sub-model parameter. For example, in one embodiment the sub-model parameter is a value for the net pressure gradient ($PG_{net}|_{MV}$) across the mitral valve during left atrium ejection, optionally a maximum or minimum value, which may also be an indicator of hemodynamic function Alternatively, the indicator of hemodynamic function may be based on one or more sub-model parameters determined for the subject. As used herein, the phrase "determining the indicator of hemodynamic function for the subject based on at least one sub-model parameter for the subject" includes but is not limited to recognizing that a determined value for a sub-model parameter is also an indicator of hemodynamic function.

In one embodiment, the lumped parameter model comprises one or more sub-models selected from a left ventricle sub-model, a left atrium sub-model, an aortic valve sub-model, a mitral valve sub-model, a systemic sub-model and a pulmonary circulation sub-model.

In one embodiment, one of the sub-models is a left ventricle sub-model and the left ventricle sub-model may be determined based on a time varying normalized elastance function, optionally modelled using a double Hill function.

In one embodiment, one of the sub-models is a left atrium sub-model and the left atrium sub-model may be defined by a time varying normalized elastance function, optionally modelled using a double Hill function.

In one embodiment, one of the sub-models is an aortic valve sub-model and the aortic valve sub-model may be defined by a time-varying net pressure gradient function across the aortic valve during left ventricle ejection, optionally wherein the aortic valve sub-model may be further defined by a function representative of aortic regurgitation.

In one embodiment, one of the sub-models is a mitral valve sub-model and the mitral valve sub-model may be defined by a net pressure gradient function across the mitral valve during left atrium ejection, optionally wherein the mitral valve sub-model may further be defined by a function representative of mitral regurgitation.

In one embodiment, one of the sub-models may be a pulmonary circulation sub-model and the pulmonary circulation sub-model may be defined by a rectified sine curve waveform with a duration ($t_{ee}$) and amplitude based on a mean flow rate of the pulmonary valve ($Q_{MPV}$).

Optionally, the embodiments described herein further comprise optimizing one or more sub-model parameters based on subject data. For example, in one embodiment the method comprises optimizing a sub-model parameter for the mean flow rate of the pulmonary valve ($Q_{MPV}$) based on minimizing the error between a sub-model parameter value of LVOT-SV determined for the subject using the lumped parameter model and a value of LVOT-SV for the subject determined using the non-invasive imaging modality.

In one embodiment, one of the sub-models is a systemic sub-model, and the systemic sub-model may be defined by sub-model parameters for systemic artery resistance ($R_{SA}$), aorta compliance ($C_{ao}$) and systemic compliance ($C_{SAC}$).

Optionally, the method may further comprise optimizing sub-model parameter values for systemic artery resistance ($R_{SA}$), aorta compliance ($C_{ao}$) and systemic compliance ($C_{SAC}$) based on minimizing the error between values of systolic and diastolic blood pressure determined for the subject using the lumped parameter model and values of systolic and diastolic blood pressure for the subject determined using a sphygmomanometer or other suitable device.

In one embodiment, the indicator of hemodynamic function is an indicator of global hemodynamic function. For example, in one embodiment the indicator of global hemodynamic function is selected from the group of a left ventricle workload, a left-ventricular end-diastolic pressure and an instantaneous left-ventricular pressure. In one embodiment, the indicator of global hemodynamic function is determined at least based on a determined sub-model parameter of at least one sub-model in the plurality of sub-models, optionally wherein the determined sub-model parameter is a determined systemic sub-model parameter.

In one embodiment, the indicator of hemodynamic function is an indicator of local hemodynamic function. For example, in one embodiment the indicator of hemodynamic function is selected from the group of a left ventricle pressure, an aorta pressure, an atrium pressure, an aortic valve pressure, a mitral valve pressure, a mitral flow rate, a left ventricle flow, an aorta flow, a left ventricle volume and a left atrial volume as well as flow, pressure and volume through the circulatory system.

Optionally, the indicator of hemodynamic function may be an indicator of heart workload. For example, in one embodiment the indicator of hemodynamic function is an integral of LV pressure and volume estimated as the area covered by a LV pressure-volume loop.

The embodiments described herein may be used for generating a patient-specific model of cardiovascular function at a first time point based on a first set of input parameters and optionally determining an indicator of hemodynamic function for the subject at a second time point based on one or more subsequent input parameters. For example, a patient-specific lumped parameter model determined using imaging data and blood pressure data may be updated at a later time point using only blood pressure data in order to determine an indicator of hemodynamic function and monitor a subject for cardiovascular disease. In one embodiment, the method comprises receiving one or more subsequent input parameters for the subject, and determining a subsequent indicator of hemodynamic function for the subject based on the at least one sub-model parameter determined based on the lumped parameter model and the plurality of input parameters, and the subsequent input parameter. In one embodiment, the subsequent input parameter is indicative of blood pressure, such as diastolic or systolic blood pressure. Accordingly, the embodiments described herein may be used for determining a change in cardiovascular disease in the subject based on a change in one or more indicators of hemodynamic function relative to one or more subsequent indicators of hemodynamic function.

The methods described herein may be used for diagnosing, monitoring or prognosing cardiovascular disease in the subject based on the indicator of hemodynamic function, optionally based on a plurality of indicators of hemodynamic function. As used herein "diagnosing, monitoring or prognosing cardiovascular disease in the subject" includes, but is not limited to, diagnosing, monitoring or prognosing C3VI as well as predicting the effect of an intervention, such as a surgical intervention, optionally an intervention for C3VI, on cardiovascular disease or dysfunction in the subject.

In some embodiments, the method may further comprise comparing the indicator of hemodynamic function for the subject to a control value. For example, in one embodiment the control value is representative of hemodynamic function in subjects with cardiovascular disease or a specific dysfunction and a similarity between the indicator of hemodynamic function for the subject and the control value is indicative of cardiovascular disease or specific dysfunction in the subject. In some embodiments, the control value may be a threshold value and an indicator of hemodynamic function below or above the control value is indicative of cardiovascular disease or specific dysfunction.

In some embodiments, cardiovascular disease may comprise complex valvular-vascular-ventricular interactions (C3VI). These may include, without limitation, valvular disease such as aortic valve stenosis, mitral valve stenosis, aortic valve regurgitation or mitral valve insufficiency, ventricular disease such as left ventricle dysfunction or heart failure, vascular disease such as hypertension, paravalvular leaks, or LV outflow tract obstruction, or changes due to surgical procedures for C3VI such as valve replacement or left ventricular reconstructive surgery.

In some embodiments, method may further comprise determining the relative contribution of one or more physiological parameters such as a C3VI disease constituents to cardiovascular disease in the subject, optionally by comparing LV workload under different conditions. For example, determining the relative contribution of one or more one C3VI disease constituents to cardiovascular disease in the subject may comprise comparing LV workload for the subject with LV workload for the subject determined using the lumped parameter model wherein one or more sub-model parameters are modified to represent a modified C3VI disease constituent, optionally a healthy or normal C3VI disease constituent. The C3VI disease constituent may be, without limitation, aortic valve stenosis, aortic regurgitation, mitral regurgitation, left ventricle hypertrophy and dysfunction, heart failure, vascular disease (like hypertension), or paravalvular leakage after intervention. In some embodiments, the methods described herein may be used to predict the effects of an intervention or treatment, such as a surgical procedure, to address a particular C3VI disease constituent by comparing indicators of hemodynamic function, optionally heart workload, under various conditions associated with modified sub-model parameters.

Accordingly, the methods described herein may further comprise selecting a treatment for the subject based on the indicator of hemodynamic function, optionally based on a plurality of indicators of hemodynamic function or based on the relative contribution of the one or more C3VI disease constituents to cardiovascular disease in the subject. Optionally, the embodiments described herein include administering a selected treatment to the subject, such as by performing a surgical procedure.

In one or more embodiments, the methods described herein comprise receiving a plurality of input parameters for the subject, such as cardiovascular imaging data and/or blood pressure data, and then determining based on the input parameters and the lumped parameter model. The input parameters may be pre-determined or stored electronically prior to being received and processed according to the embodiments described herein. Alternatively, the methods may comprise determining the plurality of input parameters for the subject by testing the subject. For example, in one embodiment the method comprises measuring or performing Doppler echocardiography and/or sphygmomanometry on the subject to determine one or more input parameters such as cardiovascular anatomical measurements and/or blood pressure data.

In one embodiment, the methods described herein may be performed using a system. For example, in one embodiment there is provided a system for determining an indicator of hemodynamic function for a subject. In one embodiment, the system comprises a memory and a processor in communication with the memory. In one embodiment, the memory comprises a lumped parameter model and the processor is configured to receive a plurality of input parameters for the subject and determine at least one sub-model parameter based on the lumped parameter model and the plurality of input parameters. In one embodiment the processor is configured to determine the indicator of hemodynamic function for the subject based on at least one sub-model parameter for the subject.

Figure 16:
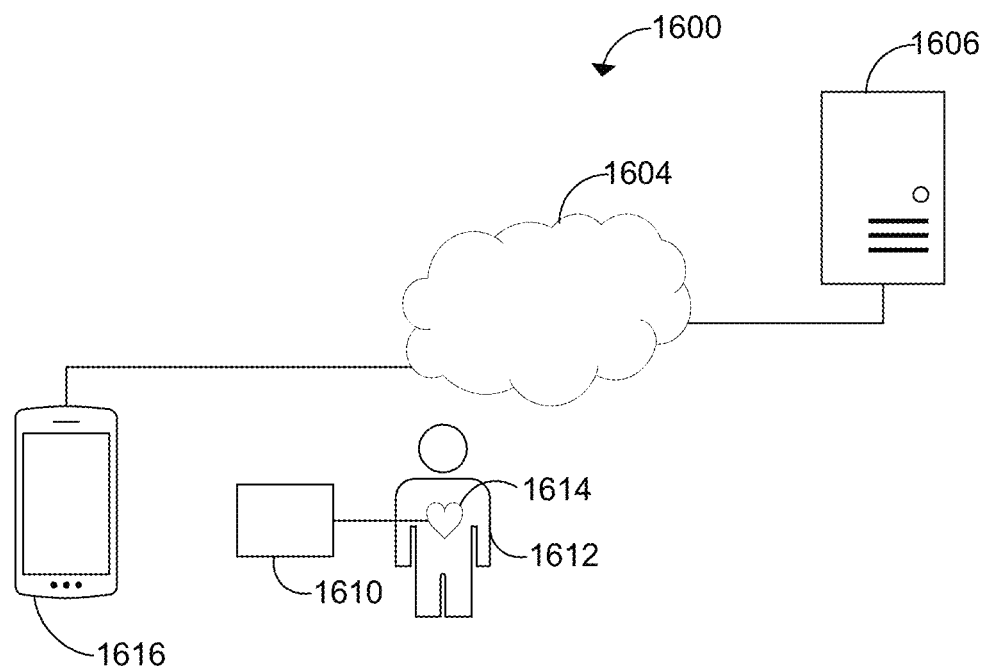
FIG. 16 shows a non-invasive system for determining an indicator of hemodynamic function in accordance with one or more embodiments.

Reference is next made to FIG. 16, there is shown a system diagram 1600 of a non-invasive system for determining an indicator of hemodynamic function. The system for determining an indicator of hemodynamic function may include one or more user devices 1616, a network 1604, and a server 1606. Also shown is a subject 1612 having a heart 1614 and one or more cardiac monitoring devices 1610.

The one or more user devices 1616 may be used by an end user to access a software application (not shown), either via a web browser or locally at device 1616. The software application may run at server 1606 and be accessible over network 1604 to the web browser at user device 1616. Alternatively, the user of user device 1616 may download an app from an app store such as the Google® Play Store or the Apple App Store. The user device 1616 may be a desktop computer, mobile device, or laptop computer. The user device 1616 may be in communication with server 1606, and may allow a user to review a user profile stored in a database at server 1606.

The user of user device 1616 may be the subject 1612, optionally being monitored by cardiac monitoring device 1610. In an alternate embodiment, a separate user such as a medical professional (not shown) may operate user device 1616 in order to determine an indicator of hemodynamic function for subject 1612.

The user device 1616 may be any two-way communication device with capabilities to communicate with other devices. The user device 1616 may be a mobile device such as mobile devices running the Google® Android® operating system or Apple® iOS® operating system.

Each user device 1616 includes and executes a client application, such as a cardiovascular modelling application, which communicates with or otherwise receives data obtained from cardiac monitoring device 1610.

The cardiovascular modelling application on user device 1616 may communicate with server 1606 using an Application Programming Interface (API) endpoint, and may send and receive data such as cardiac measurement data, sub-model parameters and an indicator of hemodynamic function.

Network 1604 may be any network or network components capable of carrying data including the Internet, Ethernet, fiber optics, satellite, mobile, wireless (e.g. Wi-Fi, WiMAX), SS7 signaling network, fixed line, local area network (LAN), wide area network (WAN), a direct point-to-point connection, mobile data networks (e.g., Universal Mobile Telecommunications System (UMTS), 3GPP Long-Term Evolution Advanced (LTE Advanced), Worldwide Interoperability for Microwave Access (WiMAX), etc.) and others, including any combination of these.

Subject 1612 may be a patient using a cardiac monitoring device 1610 in a clinical setting, or an individual who uses a cardiac monitoring device 1610 for informational purposes, such as ongoing monitoring of cardiovascular health. The subject 1612 may have a user profile on service 1606 that may remotely track the cardiac measurement data including indicators of hemodynamic function, along with measurements made by the cardiac monitoring device 1610.

Cardiac monitoring device 1610 may comprise one or more devices for monitoring the subject's heart. For example, in one embodiment the cardiac monitoring device 1610 comprises a non-invasive imaging modality. Cardiac monitoring device 1610 may include one or more different devices, such as a Doppler ultrasonograph and/or a sphygmomanometer. Data from one or more cardiac monitoring devices 1610 may be provided to the user device 1616. For example, a Doppler ultrasonograph may be used for Doppler echocardiographic analysis of the heart 1614 of subject 1612, and may provide at least one input parameter for the lumped parameter model in a software application running at user device 1616 or at server 1606. A sphygmomanometer or other similar device may also be used to obtain at least one input parameter for the lumped parameter model in a software application running at user device 1616 or at server 1606.

In one embodiment, the ultrasonograph comprises a transducer probe for sending and receiving sound waves, a processing unit for receiving an electrical signal representative of the reflected sound waves, and transducer pulse controls for changing the amplitude, frequency and duration of the pulses emitted from the transducer probe.

The at least one input parameter may be collected wirelessly from the cardiac monitoring device 1610 by the user device 1616, which may be in wireless communication using, for example, Bluetooth or another wireless data transmission protocol. Alternatively, user device 1616 may be in wired connection to the cardiac device 1610. The at least one input parameter may include a forward left ventricular outflow tract stroke volume (LVOT-SV), a heart rate, an ejection time, an ascending aorta area, a left ventricular outflow tract area, an aortic valve effective orifice area, a mitral valve effective orifice area, an indicator of aortic valve regurgitation severity and an indicator of mitral valve regurgitation severity. The at least one input parameter may further include systolic and diastolic blood pressure data. In some embodiments, one or more of the input parameters may be determined by the system, optionally user device 1616 or server 1606, based on raw or processed data obtained from cardiac monitoring device 1610, such as cardiac imaging data.

In one embodiment, the functions of the user device 1616 may be performed by the cardiac monitoring device 1610. In this embodiment, the cardiac monitoring device 1610 may provide the software application for determining an indicator of hemodynamic function.

The server 1606 is in network communication with the user device 1616. The server 1606 may have an application server and a database. The database and the application server may be provided on the same server, may be configured as virtual machines, or may be configured as containers. The server 1606 may run on a cloud provider such as Amazon® Web Services (AWS®).

The server 1606 may host a web application or an Application Programming Interface (API) endpoint that the user device 1616 or cardiac measurement device 1610 may interact with via network 1604. The requests made to the API endpoint of server 1606 may be made in a variety of different formats, such as JavaScript Object Notation (JSON) or eXtensible Markup Language (XML).

The database may store subject information including cardiac measurement data history, lumped parameter model data and hemodynamic indicator data. The database may be a Structured Query Language (SQL) such as PostgreSQL or MySQL or a not only SQL (NoSQL) database such as MongoDB.

In one embodiment, the indicator of hemodynamic function determined according to the embodiments described herein is communicated to a user. For example, in one or more embodiments, the indicator of hemodynamic function is communicated to a user by outputting the indicator on a display of user device 1616 or cardiac monitoring device 1610.

Figure 17:
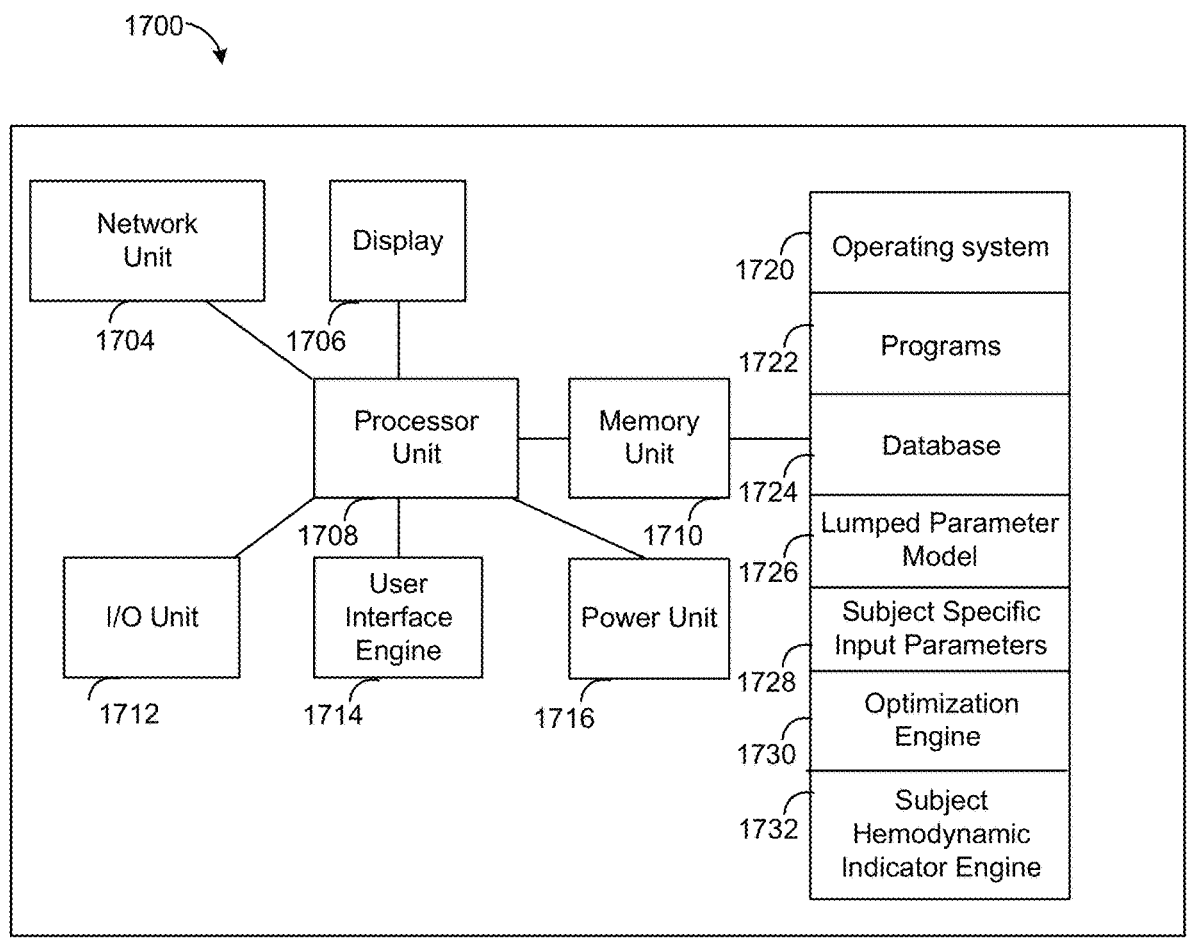
FIG. 17 shows a device for determining an indicator of hemodynamic function in accordance with one or more embodiments.

Referring next to FIG. 17, there is a device diagram 1700 of user device 1616 (see FIG. 16). In an alternate embodiment, the functionality of user device 1616 may be provided by cardiac monitoring device 1610 and the device diagram 1700 is for the cardiac monitoring device 1610 or it may be provided by server 1606 and the device diagram 1700 is for server 1606.

In one embodiment, the methods described herein may be performed using device 1700. For example, in one embodiment there is provided a device for determining an indicator of hemodynamic function for a subject.

The user device 1700 includes one or more of a network unit 1704, a display 1706, a processor unit 1708, a memory unit 1710, I/O unit 1712, a user interface engine 1714, a power unit 1716.

The network unit 1704 can include wired or wireless connection capabilities. The network unit 1704 can include a radio that communicates utilizing CDMA, GSM, GPRS or Bluetooth protocol according to standards such as IEEE 802.11a, 802.11b, 802.11g, or 802.11n. The network unit 1704 can be used by the user device 1700 to communicate with other devices or computers.

Network unit 1704 may communicate using a wireless transceiver to transmit and receive information via a local wireless connection with the cardiac monitoring device. The network unit 1704 may provide communications over the local wireless network using a protocol such as Bluetooth (BT) or Bluetooth Low Energy (BLE).

The display 1706 may be an LED or LCD based display, and may be a touch sensitive user input device that supports gestures.

The processor unit 1708 controls the operation of the user device 1700. The processor unit 1708 can be any suitable processor, controller or digital signal processor that can provide sufficient processing power depending on the configuration, purposes and requirements of the user device 1700 as is known by those skilled in the art. For example, the processor unit 1708 may be a high performance general processor. In alternative embodiments, the processor unit 1708 can include more than one processor with each processor being configured to perform different dedicated tasks. In alternative embodiments, it may be possible to use specialized hardware to provide some of the functions provided by the processor unit 1708. For example, the processor unit 1708 may include a standard processor, such as an Intel® processor, an ARM® processor or a microcontroller.

The processor unit 1708 can also execute a user interface (UI) engine 1714 that is used to generate various UIs, for example, for reporting a hemodynamic indicator to a user of the user device 1700.

The memory unit 1710 comprises software code for implementing an operating system 1720, programs 1722, database 1724, lumped parameter model 1726, subject specific input parameters 1728, optimization engine 1730, and subject hemodynamic indicator engine 1732.

The memory unit 1710 can include RAM, ROM, one or more hard drives, one or more flash drives or some other suitable data storage elements such as disk drives, etc. The memory unit 1710 is used to store an operating system 1720 and programs 1722 as is commonly known by those skilled in the art.

The I/O unit 1712 can include at least one of a mouse, a keyboard, a touch screen, a thumbwheel, a track-pad, a track-ball, a card-reader, voice recognition software and the like again depending on the particular implementation of the user device 1700. In some cases, some of these components can be integrated with one another.

The user interface engine 1714 is configured to generate interfaces for users to configure cardiac measurements, connect to the cardiac measurement device, view indicators of hemodynamic function, etc. The various interfaces generated by the user interface engine 1714 are displayed to the user on display 1706.

The power unit 1716 can be any suitable power source that provides power to the user device 1700 such as a power adaptor or a rechargeable battery pack depending on the implementation of the user device 1700 as is known by those skilled in the art.

The operating system 1720 may provide various basic operational processes for the user device 1700. For example, the operating system 1720 may be a mobile operating system such as Google® Android® operating system, or Apple® iOS® operating system, or another operating system.

The programs 1722 include various user programs so that a user can interact with the user device 1700 to perform various functions such as, but not limited to, connecting to the cardiac measurement devices and viewing indicators of hemodynamic function. In one embodiment, programs 1722 include various user programs so that a user can interact with the user device 1700 to, for example determine the relative contribution of one or more one disease constituents to cardiovascular disease in the subject, or predict the relative effect of different interventions on global and/or local indicators of hemodynamic function in the subject.

The database 1724 may be a database for storing cardiac measurement data from the cardiac measurement device, sub-model parameters, lumped parameter models and determined hemodynamic indicators of one or more subjects. The database 1724 may receive the data from the subject specific input parameters 1728 and the subject hemodynamic indicator engine 1732, and may further receive queries for information from the optimization engine 1730.

The database 1724 may be a database for storing subject specific information for the lumped parameter model 1726, including models or sub-model parameters generated by the optimization engine 1730.

The lumped parameter model 1726 may be the lumped parameter model as described herein (see e.g. FIGS. 1A and 1B). The lumped parameter model 1726 may be represented as an electrical circuit model. The lumped parameter model 1726 may including one or more time varying functions describing portions of the model. The lumped parameter model 1726 may include one or more ordinary differential equations corresponding to sub-models or sub-portions.

The subject specific input parameters 1728 are received cardiac measurement data from the cardiac measurement devices (see e.g. 1610 in FIG. 16), optionally via the wireless transceiver and the network unit 1704. The subject specific input parameters 1728 may be received and stored in database 1724. The subject specific input parameters 1728 may be supplemented with user device data and user device metadata. The subject specific input parameters 1728 may be sent to a server (see e.g. 1606 in FIG. 16). The subject specific input parameters 1728 may communicate with the cardiac measurement device wirelessly, using a wired connection, or using a computer readable media such as a flash drive or removable storage device.

The optimization engine 1730 may determine, based on cardiac measurement data including a plurality of input parameters for a subject, one or more solutions to the lumped parameter model 1726, including sub-model parameters or coefficients that describe the cardiovascular function of a subject. For example, the optimization engine 1730 may apply the method of FIG. 8 to determine the lumped parameter model 1726 solution for a subject. The solution for the subject may be stored in database 1724, and may be used subsequently to establish and evaluate a subject's cardiovascular function.

The subject hemodynamic indicator engine 1732 may determine one or more hemodynamic indicators based on the lumped parameter model 1726, subject specific input parameters 1728, and the solution for the subject to the lumped parameter model 1726 as determined by the optimization engine 1730. This may be as described in FIGS. 11A(ii), 11B(ii), 12A(ii), 12B(ii), 13A(ii), and 13B(ii). The hemodynamic indicator determined for a subject may be, for example, a single value for workload, or may define a function describing the LV pressure as function of LV volume.

In the preferred embodiment, the functions of the database 1724, lumped parameter model 1726, subject specific input parameters 1728, optimization engine 1730, and subject hemodynamic indicator engine 1732 may be performed by the user device (see e.g. 1616 in FIG. 16).

In an alternate embodiment, some or all of the functions of the database 1724, lumped parameter model 1726, subject specific input parameters 1728, optimization engine 1730, and subject hemodynamic indicator engine 1732 may be performed by the cardiac monitoring device (see e.g. 1610 in FIG. 16).

In an alternate embodiment, some or all of the functions of the database 1724, lumped parameter model 1726, subject specific input parameters 1728, optimization engine 1730, and subject hemodynamic indicator engine 1732 may be performed by the server (see e.g. 1606 in FIG. 16).

In one embodiment, the methods described herein may be performed by executing instructions on computer readable media using a computer processor. Accordingly, in one embodiment there is provided a non-transitory computer readable medium comprising computer-executable instructions for determining an indicator of hemodynamic function for a subject. In one embodiment, the computer-executable instructions when executed cause a processor to determine, based on a pre-determined lumped parameter model and a plurality of input parameters for the subject, at least one sub-model parameter and an indicator of hemodynamic function for the subject based on at least one sub-model parameter for the subject.

In one embodiment, the lumped parameter model comprises a plurality of sub-models, the plurality of sub-models defined by a set of time-varying functions comprising at least one sub-model parameter. In one embodiment, the input parameters comprise at least one input parameter obtained using a non-invasive cardiovascular imaging modality and at least one input parameter indicative of blood pressure.

The non-transitory computer readable medium may be stored a local or remote hard disk or hard drive (of any type, including electromechanical magnetic disks and solid-state disks), a memory chip, including, e.g., random-access memory (RAM) and/or read-only memory (ROM), cache(s), buffer(s), flash memory, optical memory such as CD(s) and DVD(s), floppy disks, and any other form of storage medium in or on which information may be stored for any duration. Different implementations of the disclosed method(s) may involve performing some or all the steps described herein in different orders or some or all of the steps substantially in parallel. Different implementations may involve performing some or all of the steps on different processors or the same processor, optionally wherein the processors are in networked communication. The functions or method steps may be implemented in a variety of programming languages known in the art. For example, such code or computer readable or executable instructions may be stored or adapted for storage in one or more machine-readable media, such as described above, which may be accessed by a processor-based system to execute the stored code or computer readable or executable instructions.

TABLE 1

Exemplary cardiovascular parameters used in the lumped parameter modeling to simulate all patient-specific cases.

| Description | Abbreviation | Value |
|---|---|---|
| Valve parameters | | |
| Effective orifice area | EOA | Measured using DE |
| Energy loss coefficient | $E_L Co$ | $\dfrac{(EOA)A}{A - EOA}$ <br> EOA and A are measured using DE |
| Variable resistance | $R_{AV}$ & $R_{AR}$ | $\dfrac{\rho}{2E_L Co\|_{AV}^2} Q(t)$ & $\dfrac{\rho}{2E_L Co\|_{AR}^2} Q(t)$ |
| | $R_{MV}$ & $R_{MR}$ | $\dfrac{\rho}{2EOA\|_{MV}^2} Q_{MV}(t)$ & $\dfrac{\rho}{2EOA\|_{MR}^2} Q(t)$ |

TABLE 1-continued

| | | |
|---|---|---|
| Inductance | $L_{AV}$ & $L_{AR}$ | $\dfrac{2\pi\rho}{\sqrt{2E_L Co\|_{AV}}}$ & $\dfrac{2\pi\rho}{\sqrt{2E_L Co\|_{AR}}}$ |
| | $L_{MV}$ & $L_{MR}$ | $\dfrac{M_{MV}}{EOA_{M_V}}$ & $\dfrac{M_{MV}}{EOA_{MR}}$ |
| Inertance (mitral valve) | $M_{MV}$ | Constant value: 0.53 gcm$^{-2}$ |

Systematic circulation parameters

| | | |
|---|---|---|
| Aortic resistance | $R_{ao}$ | Constant value: 0.05 mmHg·s·mL$^{-1}$ |
| Aortic compliance | $C_{ao}$ | Initial value: 0.5 mL/mmHg<br>Optimized based on brachial pressures<br>(Systolic and diastolic brachial pressures are optimization constraints) |
| Systemic vein resistance | $R_{SV}$ | 0.05 mmHg·s·mL$^{-1}$ |
| Systemic arteries and veins compliance | $C_{SAC}$ | Initial value: 2 mL/mmHg<br>Optimized based on brachial pressures<br>(Systolic and diastolic brachial pressures are optimization constraints) |
| systemic arteries resistance (including arteries, arterioles and capillaries) | $R_{SA}$ | Initial value: 0.8 mmHg·s·mL$^{-1}$<br>Optimized based on brachial pressures<br>(Systolic and diastolic brachial pressures are optimization constraints) |
| Upper body resistance | $R_{ub}$ | Adjusted to have 15% of total flow rate in healthy case[15] |
| Proximal descending aorta resistance | $R_{pda}$ | Constant value: 0.05 mmHg·s·mL$^{-1}$ |

Elastance Function*

| | | |
|---|---|---|
| Maximum Elastance | $E_{max}$ | 2.1 (LV)<br>0.17 (LA) |
| Minimum Elastance | $E_{min}$ | 0.06 (LV, LA) |
| Elastance ascending gradient | $m_1$ | 1.32 (LV, LA) |
| Elastance descending gradient | $m_2$ | 27.4 (LV)<br>13.1 (LA) |
| Elastance ascending time translation | $\tau_1$ | 0.269 T (LV)<br>0.110 T (LA) |
| Elastance descending time translation | $\tau_2$ | 0.452 T (LV)<br>0.18 T (LA) |
| Elastance Normalization | N | $\dfrac{E_{MAX} - E_{MIN}}{2}$ |

Pulmonary circulation parameters

| | | |
|---|---|---|
| Pulmonary Vein Inertance | $L_{PV}$ | Constant value: 0.0005 mmHg·s$^2$·mL$^{-1}$ |
| Pulmonary Vein Resistance | $R_{PV}$ | Constant value: 0.002 mmHg·s·mL$^{-1}$ |
| Pulmonary Vein and capillary Resistance | $R_{PVC}$ | Constant value: 0.001 mmHg·s·mL$^{-1}$ |
| Pulmonary Vein and Capillary Compliance | $C_{PVC}$ | Constant value: 40 mL/mmHg |
| Pulmonary Capillary Inertance | $L_{PC}$ | Constant value: 0.0003 mmHg·s$^2$·mL$^{-1}$ |
| Pulmonary Capillary Resistance | $R_{PC}$ | Constant value: 0.21 mmHg·s·mL$^{-1}$ |
| Pulmonary Arterial Resistance | $R_{PA}$ | Constant value: 0.01 mmHg·s·mL$^{-1}$ |
| Pulmonary Arterial Compliance | $C_{PA}$ | Constant value: 4 mL/mmHg |
| Mean Flow Rate of Pulmonary Valve | $Q_{MPV}$ | Forward LVOT-SV is the only input flow condition (measured using DE).<br>$Q_{MPV}$ is a flow parameter that was optimized so that the lump-parameter model could reproduce the desirable DE-measured Forward LVOT-SV. |

Input flow condition

| | | |
|---|---|---|
| Forward left ventricular outflow tract stroke volume | Forward LVOT-SV | Measured using DE |

TABLE 1-continued

| Output condition | | |
|---|---|---|
| Central venous pressure | $P_{CV0}$ | Constant value: 4 mmHg |
| Other | | |
| Constant blood density | ρ | Constant value: 1050 kg/m³ |
| Heart rate | HR | Measured using DE |
| Duration of cardiac cycle | T | Measured using DE |
| Systolic End Ejection time | $T_{EJ}$ | Measured using DE |
| End diastolic volume | EDV | Measured using DE |
| End systolic volume | ESV | Measured using DE |

| | Pre intervention Mean ± SD (n = 49) | 90-day post intervention Mean ± SD (n = 49) |
|---|---|---|
| Ventricular indices - DE findings | | |
| Ejection fraction, % | 53.5 ± 12.7 | 61 ± 14.6 |
| Heart rate, bpm | 70.7 ± 9.5 | 68 ± 11.8 |
| Stroke volume, mL | 48.3 ± 11.7 | 44.5 ± 15.5 |
| Valvular indices - DE findings | | |
| Aortic valve effective orifice area (cm²) | 0.58 ± 0.16 | 1.75 ± 0.4 |
| Mean aortic valve gradient, mmHg | 51.52 ± 13.6 | 11.1 ± 6.1 |
| Maximum aortic valve gradient, mmHg | 84.5 ± 21.32 | 20.4 ± 10.28 |
| Aortic valve disease type | Tricuspid: 46; Bicuspid: 3 | N/A |
| Transcatheter valve prosthetic size, mm | N/A | 26.87 ± 1.6 |
| Transcatheter valve prosthetic type | N/A | CoreValve, SAPIEN & SAPIENXT |
| Aortic valve Regurgitation ≥ grade 2 | 48% | 5% |
| Mitral valve Regurgitation ≥ grade 2 | 19% | 20% |
| Vascular indices - Sphygmomanometer | | |
| Brachial systolic blood pressure, mmHg | 139 ± 22.5 | 135 ± 16.8 |
| Brachial diastolic blood pressure, mmHg | 79 ± 11.7 | 68 ± 10.3 |
| Patient description | | |
| Mean age, years; Gender | 64.5 ± 5.5; (Female: 36%) | N/A |
| Mean weight, kg; Mean height, cm | 73.4 ± 12.8; 165.7 ± 9.6 | N/A |
| Body surface area, m² | 1.73 ± 0.14 | N/A |
| Body mass index, kg/m² | 31.9 ± 21.5 | N/A |

Example 1: Comparison of C3VI-CMF with Cardiac Catheterization Data

Study Population

Forty-nine patients with C3VI who underwent TAVR or mitral valvuloplasty (see Table 2 for patients characteristics) between 2011 and 2018 at St. Joseph's Healthcare and Hamilton Health Sciences (Hamilton, ON, Canada) and Hospital Universitario Marques de Valdecilla (IDIVAL, Santander, Spain) were retrospectively considered[2]. The protocol was reviewed and approved by the Ethics Committee of the institutions. Doppler echocardiography data were acquired at 2 time points: pre-procedure and 90-day post procedure. Echocardiograms were analyzed by senior cardiologists[2]. The model takes the following echocardiography parameters in patients as the inputs: forward left ventricular outflow tract stroke volume (Forward LVOT-SV), cardiac cycle time (T), ejection time ($T_{EJ}$), $EOA_{AV}$, $EOA_{MV}$, $A_{AO}$, $A_{LVOT}$, $EOA_{AR}$, $EOA_{MR}$. In addition, the model uses the brachial systolic and diastolic pressures measured by sphygmomanometer. Cardiac catheterizations were performed pre intervention. The pressure gradients computed using the algorithm were compared and validated against cardiac catheterization measurements in fort-nine patients with C3VI.

Statistical Analysis

All results were expressed as mean±standard deviations (SD). Statistical analyses were performed using SigmaStat software (Version 3.1, Systat Software, SanJose, CA, USA).

Results

Validation: C3VI-CMF Results vs. In Vivo Measurements

The non-invasive image-based computational mechanics tool (C3VI-CMF), described above, was validated against cardiac catheterization in 49 human subjects as follows:

Pressure waveforms: The beat-to-beat pressure calculations of C3VI-CMF were compared with cardiac catheter pressure measurements in all 49 subjects.

FIGS. 9A(i), 9A(ii), 9B(i), 9B(ii), 9C(i), and 9C(ii), shown comparisons of C3VI-CMF calculations with catheter data in 3 patients (Patients #1—FIGS. 9A(i) and 9A(ii), #2—FIGS. 9B(i) and 9B(ii) and #3—FIGS. 9C(i) and 9C(ii)). Catheter data and pressure calculated by C3VI-CMF in patients with C3VI. The beat-to-beat C3VI-CMF pressure calculation compared favorably with cardiac catheter pressure measurement in all subjects. FIGS. 9A(i), 9B(i), and 9C(i) represent catheter data from subjects #1, #2 and #3. FIGS. 9A(ii), 9B(ii) and 9C(ii) represent catheter data and modeling results for subjects #1, #2, and #3Results of C3VI-CMF show good qualitative agreements with catheter measurements in terms of both shape of the waveform, and specific wave features such as the amplitude and the timing of the systolic peak in the left ventricle and aorta. In all subjects (n=49), the calculations done by C3VI-CMF had an average RMS error of 11.8 mmHg in the LV pressure, and an average RMS error of 9.9 mmHg in the aorta pressure.

Figure 10A:
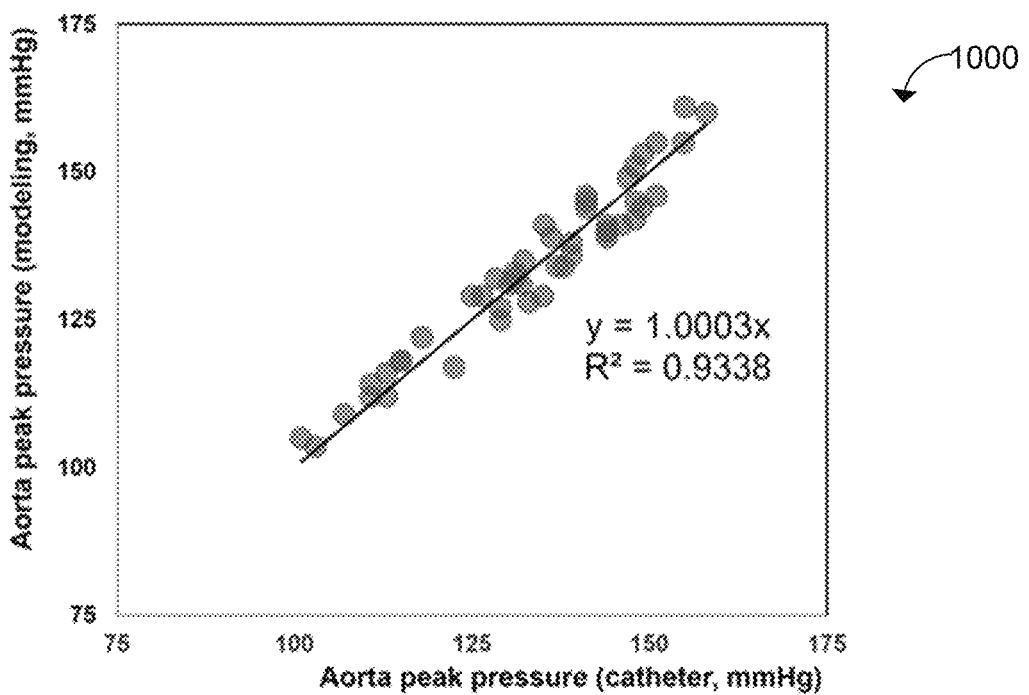
FIGS. 10A and 10B show peak pressure correlations, in accordance with one or more embodiments.
Figure 10B:
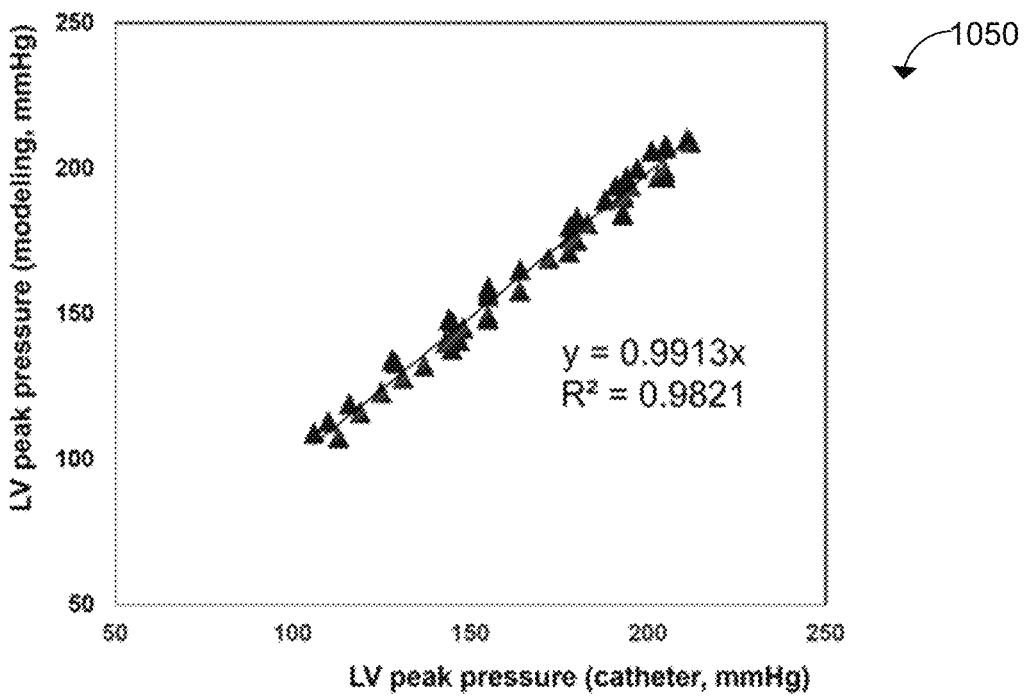

FIGS. 10A and 10B show peak pressure correlations. FIG. 10A shows the peak pressure correlation diagram for the left ventricle. FIG. 10B shows the peak pressure correlation diagram for the aorta. Peak pressures calculated by C3VI-CMF are correlated well with catheter measurements in all 49 patients with C3VI as indicated by high coefficients of determination.

Peak pressure: The Peak pressures calculated by C3VI-CMF (LV: 164.5±30.7 mmHg, aorta: 133.88±14.25 mmHg) were in close agreement with the catheter measurements (LV: 165.9±30.9 mmHg, aorta: 133.75±14.67 mmHg) in all subjects (n=49). Peak pressures resulted from C3VI-CMF correlated well with the catheter measurements as indicated by high coefficients of determination in FIGS. 10A and 10B (LV: $R^2$=0.982; aorta: $R^2$=0.933). Maximum relative errors of 4.49% and 4.33% were respectively observed in the aorta and LV pressure in all C3VI subjects, consistent with high correlations.

FIGS. 11 to 13 show samples of C3VI-CMF calculations for the same C3VI patients (Patients #1, #2 and #3) whose catheter and C3VI-CMF data for validation were shown (FIGS. 9A(i), 9A(ii), 9B(i), 9B(ii), 9C(i), and 9C(ii)) and discussed above.

Patient #1 (FIGS. 11A(i), 11A(ii), 11A(iii), 11A(iv), 11B(i), 11B(ii), 11B(iii) and 11B(iv)) underwent TAVR (Edwards biological prosthesis) and had the following conditions: Pre-TAVR (FIGS. 11A(i), 11A(ii), 11A(iii), 11A(iv)): severe aortic stenosis (EOA=0.5 cm$^2$), mild aortic regurgitation (AR), moderate to severe mitral regurgitation (MR), moderate to severe concentric hypertrophy, ejection fraction: 50%, brachial pressures: 40 and 115 mmHg, forward LV stroke volume: 54 mL; Post-TAVR (116(i), 11B(ii), 11B(iii) and 11B(iv)): aortic valve (EOA=1.6 cm$^2$), mild to moderate paravalvular leakage, moderate to severe MR, hypertension, moderate to severe concentric hypertrophy, ejection fraction: 60%, brachial pressures: 45 and 140 mmHg, forward LV stroke volume: 53 mL.

Patient #2 (FIGS. 12A(i), 12A(ii), 12A(iii), 12A(iv), 12B(i), 12B(ii), 12B(iii) and 12B(iv)) underwent TAVR (Edwards biological prosthesis) and had the following conditions: Pre-TAVR (FIGS. 12A(i), 12A(ii), 12A(iii), 12A(iv)): severe aortic stenosis (EOA=0.55 cm$^2$), mild aortic regurgitation (AR), mild mitral regurgitation (MR), severe concentric hypertrophy, ejection fraction: 60-65%, brachial pressures: 50 and 135 mmHg, forward LV stroke volume: 52 mL; Post-TA VR (12B(i), 12B(ii), 12B(iii) and 12B(iv)): aortic valve (EOA=1.45 cm$^2$), trace MR, hypertension, severe concentric hypertrophy, ejection fraction: 60%, brachial pressures: 90 and 150 mmHg, forward LV stroke volume: 46 mL.

Patient #3 (FIGS. 13A(i), 13A(ii), 13(iii), 13A(iv), 13B(i), 13B(ii), 13B(iii) and 13B(iv)) underwent mitral dilatation (valvuloplasty) and had the following conditions: Pre-valvuloplasty (FIGS. 13A(i), 13A(ii), 13A(iii), 13A(iv)): mitral valve stenosis (EOA=1 cm$^2$), No MR, moderate AS (EOA=1.5 cm$^2$), mild AR (REOA=0.05 cm$^2$), ejection fraction: 55-60%, forward LV stroke volume: 46 mL, and brachial pressures: 70 and 105 mmHg; Post-valvuloplasty (FIGS. 13B(i), 13B(ii), 13B(iii), 13B(iv)): mitral valve stenosis (EOA=1.5 cm$^2$), mild to moderate MR (REOA=0.1 cm$^2$), moderate AS (EOA=1.5 cm$^2$), mild AR (REOA=0.05 cm$^2$), ejection fraction: 55-60%, forward LV stroke volume: 48 mL, and brachial pressures: 62 and 100 mmHg.

Metrics of Cardiac Function.

In the presence of C3VI, the heart is overloaded since the healthy instantaneous LV pressure and/or flow are altered. Currently, the inventor is not aware of any other methods that can invasively or non-invasively quantify the heart workload (global function) and provide contribution breakdown of each component of the cardiovascular system. This is especially crucial in C3VI because quantifications of the LV workload and its breakdown are vital to guide prioritizing interventions.

FIGS. 11 and 12 show the pre and post intervention LV workload in C3VI Patients #1 & #2 who received TAVR. Pre intervention, untreated aortic stenosis increased the burden on the LV due to the augmented flow resistance which causes a LV pressure overload in the pre-intervention status. Post intervention, TAVR was accompanied by reduction in LV workload in both patients reducing the LV workload (by 27% and 33.7% in Patient #1 and #2, respectively). FIG. 13 shows LV workload in Patient #3 in pre and post valvuloplasty status. Instead of improving the heart condition by reducing the LV workload, valvuloplasty caused an increase in the LV workload due to worsening the mitral regurgitation. FIGS. 11 to 13 demonstrate that in all three patients with various C3VI disease combinations, C3VI-CMF was able to quantify the heart workload (global hemodynamics).

Figure 14A:
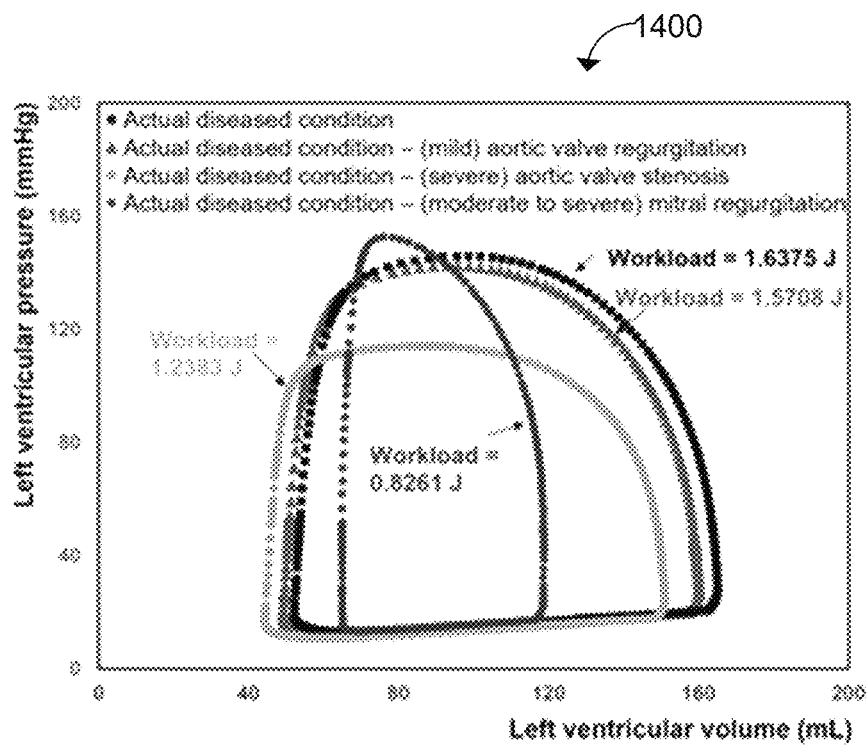
FIGS. 14A and 14B show examples of workload breakdown analysis and prediction for effects of interventions in Patient #1, in accordance with one or more embodiments.
Figure 14B:
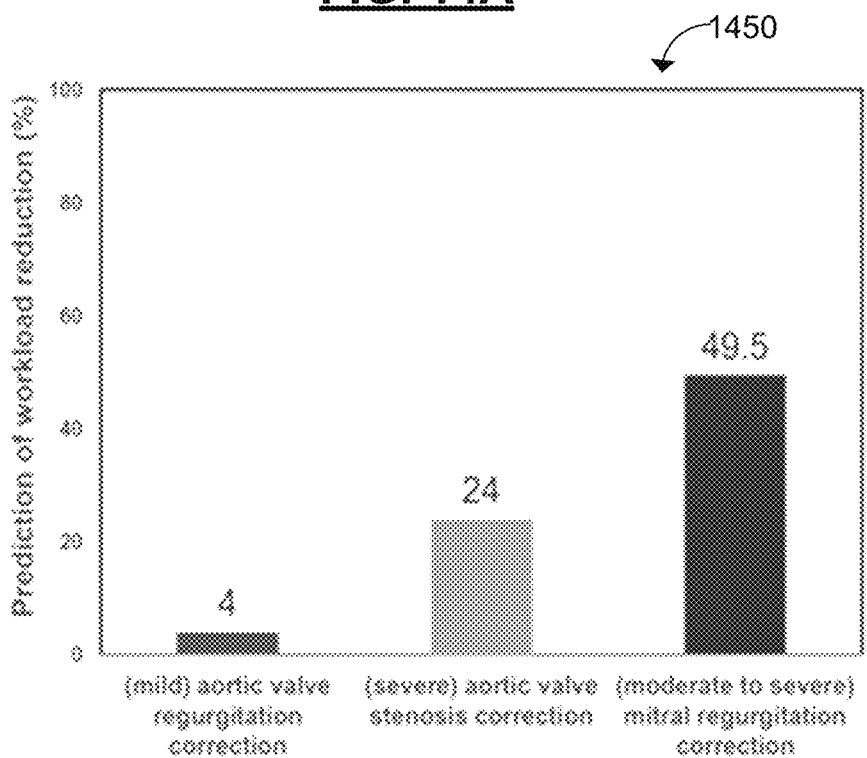

FIGS. 14A and 14B, show examples of calculations for analyzing the breakdown of the contributions of the disease constituents on the LV workload in Patient #1. This may include determining an indicator of hemodynamic function. Referring to FIG. 14B, a P-V diagram 1450 is shown of the actual diseased condition and prediction of several valve interventions. Referring to FIG. 14A, a predicted percent decrease in the left ventricle workload following valve interventions is shown. In order to plan valve interventions, each of the valvular disease constituents were replaced by the normal condition one-at-a-time and the LV workload was calculated and shown in FIG. 14A. Both mitral valve regurgitation (49.5% increase) and aortic valve stenosis (24% increase) had substantial contributions to increasing the workload. According to this analysis, correcting of mitral valve regurgitation should have the highest priority in this patient.

In the pre-intervention state, this patient had severe calcific aortic stenosis, mild aortic regurgitation, moderate to severe mitral regurgitation and concentric hypertrophy. In order to plan valve interventions, each of the valvular disease constituents were replaced by the normal condition one-at-a-time and the LV workload was calculated and shown in FIG. 14A. As shown in FIG. 14B, both mitral valve regurgitation (49.5% increase) and aortic valve stenosis (24% increase) had substantial contributions to increasing the workload. However, because mitral valve regurgitation had the greatest contribution, correcting it should have had the highest priority in the sequence of interventions. Considering the conditions of this patient, the decision of whether to also perform mitral intervention at the time of aortic valve intervention might have been carefully evaluated and considered. However, in reality, this patient only underwent transcatheter aortic valve replacement, TAVR (FIG. 11). The presented simulation results (FIGS. 14A and 14B) predict that fixing aortic valve stenosis alone can reduce the workload by 24% which agrees with the actual measurement data post-intervention (FIG. 11) in this patient (workload was reduced by 18% after TAVR).

Discussion

Due to the wide inter-subject variability in cardiovascular anatomy and pathophysiology, it is desirable to design individualized treatment plans based on the diagnosis data and the predictions made about individuals' risk of the intervention. The C3VI-CMF framework described herein provides a patient-specific non-invasive diagnostic, monitoring, and predictive tool that can investigate and quantify effects of C3VI constituents on the heart function, and the circulatory system. The basis of C3VI-CMF may be calculations of the local hemodynamics (detailed information of the fluid dynamics of the circulatory system, e.g., flow and pressure in different regions) and global hemodynamics (the heart workload). This tool may provide the breakdown of the effects of disease constituents on the global function of the heart as well so it can help predicting the effects of interventions and planning for the sequence of interventions. C3VI-CMF may be capable of tracking cardiac and vascular state based on accurate time-varying models that reproduce physiological responses. While this information is important for effectively using advanced therapies to improve clinical outcomes and guiding interventions in C3VI patients, it is currently accessible in a clinic setting.

The method was evaluated under pathophysiologic conditions and its performance was assessed in forty-nine C3VI patients with a substantial inter- and intra-patient variability with a wide range of disease. The results demonstrate not only repeatability but also validity even in different physiologic conditions (see FIGS. 9 and 10; Table 2). This demonstrates the ability of C3VI-CMF to track changes in both cardiac, and vascular states. C3VI-CMF purposefully uses reliable non-invasive input parameters to continuously calculate patient-specific hemodynamics quantities to be used for diagnosis, monitoring, and prediction of cardiac function and circulatory state with direct clinical relevance.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

1. Heart disease and stroke statistics—at-a-glance. American Heart Association (2015).
2. Keshavarz-Motamed, Z. et al. Quantification and systematic differentiation of impact of paravalvular leaks following transcatheter aortic valve replacement. Journal of American College of Cardiology. *J. Am. Coll. Cardiol.* Under review, (2019).
3. Sotiropoulos, F., Le, T. B. & Gilmanov, A. Fluid mechanics of heart valves and their replacements. *Annu. Rev. Fluid Mech.* 48, 259-283 (2016).
4. Généreux, P. et al. Paravalvular leak after transcatheter aortic valve replacement: the new Achilles' heel? A comprehensive review of the literature. *J. Am. Coll. Cardiol.* 61, 1125-1136 (2013).
5. Nombela-Franco, L. et al. Significant mitral regurgitation left untreated at the time of aortic valve replacement: a comprehensive review of a frequent entity in the transcatheter aortic valve replacement era. *J. Am. Coll. Cardiol.* 63, 2643-2658 (2014).
6. Blanke, P. et al. Predicting LVOT Obstruction in Transcatheter Mitral Valve Implantation: Concept of the Neo-LVOT. *JACC Cardiovasc. Imaging* (2016).
7. Elmariah, S. et al. Outcomes of Transcatheter and Surgical Aortic Valve Replacement in High-Risk Patients With Aortic Stenosis and Left Ventricular Dysfunction Results From the Placement of Aortic Transcatheter Valves (PARTNER) Trial (Cohort A). *Circ. Cardiovasc. Interv.* 6, 604-614 (2013).
8. Richter, Y. & Edelman, E. R. Cardiology is flow. *Circulation* 113, 2679-2682 (2006).
9. Nichols, W., O'Rourke, M. & Vlachopoulos, C. *McDonald's blood flow in arteries: theoretical, experimental and clinical principles.* (CRC Press, 2011).
10. Trip, R., Kuik, D. J., Westerweel, J. & Poelma, C. An experimental study of transitional pulsatile pipe flow. *Phys. Fluids 1994-Present* 24, 014103 (2012).
11. Di Carli, M. F., Geva, T. & Davidoff, R. The Future of Cardiovascular Imaging. *Circulation* 133, 2640-2661 (2016.
12. Casas, B. et al. Bridging the gap between measurements and modelling: a cardiovascular functional avatar. *Sci. Rep.* 7, 6214 (2017).
13. Duanmu, Z., Yin, M., Fan, X., Yang, X. & Luo, X. A patient-specific lumped-parameter model of coronary circulation. in *Scientific Reports* (2018). doi:10.1038/s41598-018-19164-w
14. Marsden, A. L. Simulation based planning of surgical interventions in pediatric cardiology. *Phys. Fluids 1994-Present* 25, 101303 (2013).
15. Keshavarz-Motamed, Z. et al. Elimination of transcoarctation pressure gradients has no impact on left ventricular function or aortic shear stress post intervention in patients with mild coarctation. *JACC Cardiovasc. Interv.* 9, 1953-1965 (2016).
16. Taylor, C. A. & Steinman, D. A. Image-based modeling of blood flow and vessel wall dynamics: applications, methods and future directions. *Ann. Biomed. Eng.* 38, 1188-1203 (2010).
17. Omran, H. et al. Silent and apparent cerebral embolism after retrograde catheterisation of the aortic valve in valvular stenosis: a prospective, randomised study. *The Lancet* 361, 1241-1246 (2003).
18. Elkins, C. J. & Alley, M. T. Magnetic resonance velocimetry: applications of magnetic resonance imaging in the measurement of fluid motion. *Exp. Fluids* 43, 823-858 (2007).
19. Kilner, P. J., Gatehouse, P. D. & Firmin, D. N. Flow measurement by magnetic resonance: a unique asset worth optimising. *J. Cardiovasc. Magn. Reson.* 9, 723-728 (2007).
20. Chaudhry, Q. A. A Gaussian function model for simulation of complex environmental sensing. *Complex Adapt. Syst. Model.* 3, 3 (2015).
21. Pironet, A. et al. Simulation of Left Atrial Function Using a Multi-Scale Model of the Cardiovascular System. *PLOS ONE* 8, e65146 (2013).
22. McDowell, S. A. C. A Simple Derivation of the Boltzmann Distribution. *J. Chem. Educ.* 76, 1393 (1999).

23. Mynard, J. P., Davidson, M. R., Penny, D. J. & Smolich, J. J. A simple, versatile valve model for use in lumped parameter and one-dimensional cardiovascular models. *Int. J. Numer. Methods Biomed. Eng.* 28, 626-641 (2012).

24. Broomé, M., Maksuti, E., Bjällmark, A., Frenckner, B. & Janerot-Sjöberg, B. Closed-loop real-time simulation model of hemodynamics and oxygen transport in the cardiovascular system. *Biomed. Eng. Online* 12, 69 (2013).

25. Moss, R. L., Razumova, M. & Fitzsimons, D. P. Myosin crossbridge activation of cardiac thin filaments: implications for myocardial function in health and disease. *Circ. Res.* 94, 1290-1300 (2004).

26. Ferrell, J. E. Q&A: Cooperativity. *J. Biol.* 8, 53 (2009).

27. Stergiopulos, N., Meister, J. J. & Westerhof, N. Determinants of stroke volume and systolic and diastolic aortic pressure. *Am. J. Physiol.* 270, H2050-2059 (1996).

28. Gleason, W. L. & Braunwald, E. Studies on the first derivative of the ventricular pressure pulse in man. *J. Clin. Invest.* 41, 80-91 (1962).

29. Werf, F. V. de et al. Diastolic properties of the left ventricle in normal adults and in patients with third heart sounds. *Circulation* 69, 1070-1078 (1984).

30. Kass, D. A., Midei, M., Graves, W., Brinker, J. A. & Maughan, W. L. Use of a conductance (volume) catheter and transient inferior vena caval occlusion for rapid determination of pressure-volume relationships in man. *Cathet. Cardiovasc. Diagn.* 15, 192-202 (1988).

31. Takeuchi, M., Odake, M., Takaoka, H., Hayashi, Y. & Yokoyama, M. Comparison between preload recruitable stroke work and the end-systolic pressure—volume relationship in man. *Eur. Heart J.* 13, 80-84 (1992).

32. Senzaki, H., Chen, C. H. & Kass, D. A. Single-beat estimation of end-systolic pressure-volume relation in humans. A new method with the potential for noninvasive application. *Circulation* 94, 2497-2506 (1996).

33. Brown, K. A. & Ditchey, R. V. Human right ventricular end-systolic pressure-volume relation defined by maximal elastance. *Circulation* 78, 81-91 (1988).

34. Dell'Italia, L. J. & Walsh, R. A. Application of a time varying elastance model to right ventricular performance in man. *Cardiovasc. Res.* 22, 864-874 (1988).

35. Maniar, H. S. et al. Impact of pericardial restraint on right atrial mechanics during acute right ventricular pressure load. *Am. J. Physiol. Heart Circ. Physiol.* 284, H350-357 (2003).

36. Liang, F., Takagi, S., Himeno, R. & Liu, H. Multi-scale modeling of the human cardiovascular system with applications to aortic valvular and arterial stenoses. *Med. Biol. Eng. Comput.* 47, 743-755 (2009).

37. Tanné, D., Kadem, L., Rieu, R. & Pibarot, P. Hemodynamic impact of mitral prosthesis-patient mismatch on pulmonary hypertension: an in-silico study. *J. Appl. Physiol.* 105, 1916-1926 (2008).

38. Pibarot, P., Hahn, R. T., Weissman, N. J. & Monaghan, M. J. Assessment of paravalvular regurgitation following TAVR: a proposal of unifying grading scheme. *JACC Cardiovasc. Imaging* 8, 340-360 (2015).

39. Zoghbi, W. A. et al. Recommendations for evaluation of the severity of native valvular regurgitation with two-dimensional and doppler echocardiography. *J. Am. Soc. Echocardiogr.* 16, 777-802 (2003).

I claim:

1. A non-invasive method for determining an indicator of hemodynamic function for a subject, the method comprising:

providing a lumped parameter model, the lumped parameter model comprising a plurality of sub-models, the plurality of sub-models defined by a set of time-varying functions comprising at least one sub-model parameter, wherein one of the sub-models is a left ventricle sub-model and the left ventricle sub-model is determined based on a time varying normalized elastance function;

one of the sub-models is a left atrium sub-model and the left atrium sub-model is defined by the time varying normalized elastance function;

one of the sub-models is an aortic valve sub-model and the aortic valve sub-model is defined by a first time-varying net pressure gradient function across the aortic valve during left ventricle ejection; or one of the sub-models is a mitral valve sub-model and the mitral valve sub-model is defined by a second time-varying net pressure gradient function across the mitral valve during left atrium ejection;

receiving a plurality of input parameters for the subject, the input parameters comprising at least one input parameter obtained using a non-invasive cardiovascular imaging modality and at least one input parameter indicative of blood pressure;

determining the at least one sub-model parameter in the plurality of sub-models for the subject based on the lumped parameter model and the plurality of input parameters; and determining the indicator of hemodynamic function for the subject based on at least one sub-model parameter for the subject.

2. The method of claim 1, wherein the non-invasive cardiovascular imaging modality is Doppler echocardiography.

3. The method of claim 1, wherein the at least one input parameter obtained using the non-invasive cardiovascular imaging modality comprises at least one selected from a forward left ventricular outflow tract stroke volume (LVOT-SV), a heart rate, an ejection time, an ascending aorta area, a left ventricular outflow tract area, an aortic valve effective orifice area, a mitral valve effective orifice area, an indicator of aortic valve regurgitation severity and an indicator of mitral valve regurgitation severity and the at least one input parameter indicative of blood pressure comprises a diastolic blood pressure and a systolic blood pressure.

4. The method of claim 1, wherein the time varying normalized elastance function is modelled using a double Hill function.

5. The method of claim 1, wherein one of the sub-models is a pulmonary circulation sub-model and the pulmonary circulation sub-model is defined by a rectified sine curve waveform with a duration ($t_{ee}$) and amplitude based on a mean flow rate of the pulmonary valve ($Q_{MPV}$) and the method further comprises optimizing the at least one sub-model parameter for the mean flow rate of the pulmonary valve ($Q_{MPV}$) based on minimizing the error between a sub-model parameter value of LVOT-SV determined for the subject using the lumped parameter model and a value of LVOT-SV for the subject determined using the non-invasive cardiovascular imaging modality.

6. The method of claim 1, wherein one of the sub-models is a systemic sub-model, and the systemic sub-model is defined by sub-model parameters for a systemic artery resistance ($R_{SA}$), an aorta compliance ($C_{ao}$) and a systemic compliance ($C_{SAC}$) and the method further comprises optimizing sub-model parameter values for the systemic artery resistance ($R_{SA}$), the aorta compliance ($C_{ao}$) and the systemic compliance ($C_{SAC}$) based on minimizing the error between values of systolic and diastolic blood pressure determined for the subject using the lumped parameter model and the values of systolic and diastolic blood pressure for the subject determined using a sphygmomanometer.

7. The method of claim 1, wherein:
the indicator of hemodynamic function comprises an indicator of global hemodynamic function selected from the group of a left ventricle workload, a left-ventricular end-diastolic pressure and an instantaneous left-ventricular pressure; and
the indicator of global hemodynamic function is determined at least based on the determined sub-model parameter of at least one sub-model in the plurality of sub-models.

8. The method of claim 1, wherein:
the indicator of hemodynamic function comprises an indicator of local hemodynamic function selected from the group of a left ventricle pressure, an aorta pressure, an atrium pressure, an aortic valve pressure, a mitral valve pressure, a mitral flow rate, a left ventricle flow, an aorta flow, a left ventricle volume, a left atrial volume, and flow, pressure and volume through the circulatory system; and
the indicator of local hemodynamic function is determined based on the determined sub-model parameter of at least one sub-model in the plurality of sub-models.

9. The method of claim 1, further comprising diagnosing, monitoring or prognosing cardiovascular disease in the subject based on the indicator of hemodynamic function.

10. The method of claim 9, wherein the cardiovascular disease comprises complex valvular-vascular-ventricular interactions (C3VI), optionally the C3VI including:
valvular disease such as aortic valve stenosis, mitral valve stenosis, aortic valve regurgitation or mitral valve insufficiency;
ventricular disease such as left ventricle (LV) dysfunction or heart failure;
vascular disease such as hypertension;
paravalvular leaks;
LV outflow tract obstruction; or
changes due to surgical procedures for C3VI such as valve replacement or left ventricular reconstructive surgery.

11. The method of claim 10, further comprising determining the relative contribution of one or more C3VI disease constituents to the cardiovascular disease in the subject, optionally by comparing LV workload.

12. The method of claim 11, wherein determining the relative contribution of the one or more C3VI disease constituents to the cardiovascular disease in the subject comprises comparing the LV workload for the subject with LV workload for the subject determined using the lumped parameter model wherein the at least one sub-model parameter is modified to represent a modified C3VI disease constituent, optionally a healthy or normal C3VI disease constituent.

13. The method of claim 12, wherein the one or more C3VI disease constituents are aortic valve stenosis, aortic regurgitation, mitral stenosis, mitral regurgitation, left ventricle hypertrophy and dysfunction, heart failure, vascular disease, or paravalvular leakage after intervention, optionally the vascular disease being hypertension.

14. The method of claim 9, further comprising selecting a treatment for the subject based on the indicator of hemodynamic function, optionally based on a plurality of indicators of hemodynamic function that includes the indicator of hemodynamic function; or based on the relative contribution of the one or more complex valvular-vascular-ventricular interactions (C3VI) disease constituents to the cardiovascular disease in the subject.

15. The method of claim 9, wherein diagnosing, monitoring or prognosing the cardiovascular disease in the subject comprises determining a prediction of an intervention effect for the subject and the indicator of hemodynamic function is the prediction of the intervention effect for the subject, the method comprising determining the indicator of hemodynamic function based on one or more of:
an indicator of global hemodynamic function determined for the subject, optionally heart workload;
a relative contribution of one or more one disease constituents to the indicator of global hemodynamic function for the subject; and
an indicator of local hemodynamic function determined for the subject, wherein the indicator of local hemodynamic function provides information on the fluid dynamics of the circulatory system for the subject.

16. The method of claim 1, wherein receiving the plurality of input parameters for the subject comprises performing the non-invasive cardiovascular imaging modality, optionally Doppler echocardiography; and sphygmomanometry, on the subject.

17. A system for determining an indicator of hemodynamic function for a subject, the system comprising:
a memory, the memory comprising:
a lumped parameter model, the lumped parameter model comprising a plurality of sub-models comprising at least one sub-model parameter, the plurality of sub-models defined by a set of time-varying functions comprising the at least one sub-model parameter, wherein
one of the sub-models is a left ventricle sub-model and the left ventricle sub-model is determined based on a time varying normalized elastance function;
one of the sub-models is a left atrium sub-model and the left atrium sub-model is defined by the time varying normalized elastance function;
one of the sub-models is an aortic valve sub-model and the aortic valve sub-model is defined by a first time-varying net pressure gradient function across the aortic valve during left ventricle ejection; or
one of the sub-models is a mitral valve sub-model and the mitral valve sub-model is defined by a second time-varying net pressure gradient function across the mitral valve during left atrium ejection;
a processor in communication with the memory, the processor configured to:
receive a plurality of input parameters for the subject, the input parameters comprising at least one input parameter obtained using a non-invasive imaging modality and at least one input parameter indicative of blood pressure;
determine the at least one sub-model parameter in the plurality of sub-models for the subject based on the lumped parameter model and the plurality of input parameters; and
determine the indicator of hemodynamic function for the subject based on at least one sub-model parameter for the subject.

18. A non-transitory computer readable medium comprising computer-executable instructions for determining an indicator of hemodynamic function for a subject, wherein the computer-executable instructions when executed cause a processor to determine the indicator of hemodynamic function based on a lumped parameter model and a plurality of input parameters for the subject, the lumped parameter model comprising a plurality of sub-models, the plurality of sub-models defined by a set of time-varying functions comprising at least one sub-model parameter, and the plurality of input parameters for the subject comprising at least one input parameter obtained using a non-invasive cardiovascular imaging modality and at least one input parameter indicative of blood pressure, wherein
- one of the sub-models is a left ventricle sub-model and the left ventricle sub-model is determined based on a time varying normalized elastance function;
- one of the sub-models is a left atrium sub-model and the left atrium sub-model is defined by the time varying normalized elastance function;
- one of the sub-models is an aortic valve sub-model and the aortic valve sub-model is defined by a first time-varying net pressure gradient function across the aortic valve during left ventricle election; or
- one of the sub-models is a mitral valve sub-model and the mitral valve sub-model is defined by a second time-varying net pressure gradient function across the mitral valve during left atrium ejection.

\* \* \* \* \*